(12) United States Patent
Linhardt et al.

(10) Patent No.: US 9,307,901 B1
(45) Date of Patent: Apr. 12, 2016

(54) METHODS FOR LEAVING A CHANNEL IN A POLYMER LAYER USING A CROSS-LINKED POLYMER PLUG

(71) Applicant: Verily Life Sciences LLC, Mountain View, CA (US)

(72) Inventors: Jeffrey George Linhardt, Pleasanton, CA (US); Zenghe Liu, Alameda, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 353 days.

(21) Appl. No.: 13/931,385

(22) Filed: Jun. 28, 2013

(51) Int. Cl.
 *A61B 5/145* (2006.01)
 *A61B 3/10* (2006.01)
 *B05D 5/00* (2006.01)
(52) U.S. Cl.
 CPC .. *A61B 3/101* (2013.01); *B05D 5/00* (2013.01)
(58) Field of Classification Search
 CPC ............................ A61B 5/14514; A61B 5/1477
 USPC .......................................... 427/2.12; 600/319
 See application file for complete search history.

(56) References Cited

U.S. PATENT DOCUMENTS

| | | | |
|---|---|---|---|
| 3,958,560 A * | 5/1976 | March | A61B 5/14558 340/870.28 |
| 4,014,321 A | 3/1977 | March | |
| 4,055,378 A | 10/1977 | Feneberg et al. | |
| 4,122,942 A | 10/1978 | Wolfson | |
| 4,136,250 A | 1/1979 | Mueller et al. | |
| 4,143,949 A | 3/1979 | Chen | |
| 4,153,641 A | 5/1979 | Deichert et al. | |
| 4,214,014 A | 7/1980 | Hofer et al. | |
| 4,309,085 A | 1/1982 | Morrison | |
| 4,312,575 A | 1/1982 | Peyman et al. | |

(Continued)

FOREIGN PATENT DOCUMENTS

| | | |
|---|---|---|
| EP | 0369942 | 5/1990 |
| EP | 0686372 | 12/1995 |

(Continued)

OTHER PUBLICATIONS

Chu et al. Soft contact lens biosensor for in situ monitoring of tear glucose as non-invasive blood sugar assessment. Talanta vol. 83, Issue 3, Jan. 15, 2011 pp. 960-965.*

(Continued)

*Primary Examiner* — Cachet Sellman
(74) *Attorney, Agent, or Firm* — McDonnell Boehnen Hulbert & Berghoff LLP

(57) ABSTRACT

A method may involve forming a cross-linked polymer plug over a sensor located on a structure, such that the sensor is covered by the cross-linked polymer plug. The sensor is configured to detect an analyte. The method may involve forming a first polymer layer, which defines a posterior side of an eye-mountable device. Further, the method may involve positioning the structure on the first polymer layer. Still further, the method may involve forming a second polymer layer over the first polymer layer and the structure to provide a partially-fabricated device. The second polymer layer defines an anterior side of the eye-mountable device. The method may also involve soaking the partially-fabricated device in a fluid, such that the cross-linked polymer plug swells out of the partially-fabricated device to leave a channel in the second polymer layer, wherein the sensor is configured to receive the analyte via the channel.

10 Claims, 13 Drawing Sheets

(56) References Cited

U.S. PATENT DOCUMENTS

| | | |
|---|---|---|
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint et al. |
| 6,087,941 A | 7/2000 | Ferraz |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 6,982,058 B2 | 1/2006 | Jacobson |
| 7,018,040 B2 | 3/2006 | Blum et al. |
| 7,131,945 B2 | 11/2006 | Fink et al. |
| 7,169,106 B2 * | 1/2007 | Fleischman .............. A61B 3/16 600/399 |
| 7,308,317 B1 | 12/2007 | Okandan et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,901,706 B2 | 3/2011 | Lally et al. |
| 7,907,931 B2 | 3/2011 | Hartigan et al. |
| 7,910,934 B2 | 3/2011 | Kim et al. |
| 7,926,940 B2 | 4/2011 | Blum et al. |
| 7,927,519 B2 * | 4/2011 | Domschke .......... A61B 5/14532 264/1.31 |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,131,333 B2 | 3/2012 | Chapoy et al. |
| 8,142,016 B2 | 3/2012 | Legerton et al. |
| 8,224,415 B2 | 7/2012 | Budiman |
| 8,241,574 B2 | 8/2012 | Burles et al. |
| 8,258,635 B2 | 9/2012 | Greenburg et al. |
| 8,385,998 B2 | 2/2013 | Zhang et al. |
| 8,425,759 B2 | 4/2013 | Wilsey |
| 8,506,740 B2 | 8/2013 | Say |
| 8,880,139 B1 * | 11/2014 | Etzkorn ............. G01N 27/3271 204/403.01 |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2006/0183986 A1 | 8/2006 | Rice et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0109175 A1 | 5/2010 | Pugh et al. |
| 2010/0110372 A1 | 5/2010 | Pugh et al. |
| 2010/0113901 A1 * | 5/2010 | Zhang ................ A61B 5/14532 600/319 |
| 2010/0133510 A1 | 6/2010 | Kim et al. |
| 2010/0249548 A1 | 9/2010 | Muller |
| 2010/0265680 A1 | 10/2010 | Tai et al. |
| 2010/0297016 A1 | 11/2010 | Geddes et al. |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0155587 A1 | 6/2011 | Shacham-Diamand et al. |
| 2011/0157541 A1 | 6/2011 | Peyman |

(56) References Cited

U.S. PATENT DOCUMENTS

| | | | |
|---|---|---|---|
| 2011/0157544 | A1 | 6/2011 | Pugh et al. |
| 2011/0184271 | A1 | 7/2011 | Veciana et al. |
| 2011/0274680 | A1 | 11/2011 | Mazed et al. |
| 2011/0286064 | A1 | 11/2011 | Burles et al. |
| 2011/0298794 | A1 | 12/2011 | Freedman |
| 2012/0026458 | A1 | 2/2012 | Qiu et al. |
| 2012/0038881 | A1 | 2/2012 | Amirparviz et al. |
| 2012/0041287 | A1 | 2/2012 | Goodall et al. |
| 2012/0041552 | A1 | 2/2012 | Chuck et al. |
| 2012/0069254 | A1 | 3/2012 | Burton |
| 2012/0075168 | A1 | 3/2012 | Osterhout et al. |
| 2012/0075574 | A1 | 3/2012 | Pugh et al. |
| 2012/0078071 | A1 | 3/2012 | Bohm et al. |
| 2012/0088258 | A1 | 4/2012 | Bishop et al. |
| 2012/0092612 | A1 | 4/2012 | Binder |
| 2012/0109296 | A1 | 5/2012 | Fan |
| 2012/0177576 | A1 | 7/2012 | Hu |
| 2012/0201755 | A1 | 8/2012 | Rozakis et al. |
| 2012/0245444 | A1 | 9/2012 | Otis et al. |
| 2012/0259188 | A1 | 10/2012 | Besling |
| 2012/0310151 | A1 | 12/2012 | Takahata et al. |
| 2013/0222759 | A1 | 8/2013 | Pugh et al. |
| 2013/0243655 | A1 | 9/2013 | Li et al. |
| 2014/0343387 | A1* | 11/2014 | Pugh ............... A61B 5/6821 600/365 |

FOREIGN PATENT DOCUMENTS

| | | |
|---|---|---|
| EP | 1061874 | 12/2000 |
| EP | 1818008 | 8/2007 |
| EP | 1947501 | 7/2008 |
| EP | 1617757 | 8/2009 |
| EP | 2457122 | 5/2012 |
| WO | 95/04609 | 2/1995 |
| WO | 01/16641 | 3/2001 |
| WO | 01/34312 | 5/2001 |
| WO | 03/065876 | 8/2003 |
| WO | 2004/060431 | 7/2004 |
| WO | 2004/064629 | 8/2004 |
| WO | 2006/015315 | 2/2006 |
| WO | 2009/094643 | 7/2009 |
| WO | 2010/105728 | 9/2010 |
| WO | 2010/133317 | 11/2010 |
| WO | 2011/011344 | 1/2011 |
| WO | 2011/034592 | 3/2011 |
| WO | 2011/035228 | 3/2011 |
| WO | 2011/035262 | 3/2011 |
| WO | 2011/083105 | 7/2011 |
| WO | 2011/163080 | 12/2011 |
| WO | 2012/035429 | 3/2012 |
| WO | 2012/037455 | 3/2012 |
| WO | 2012/051167 | 4/2012 |
| WO | 2012/051223 | 4/2012 |
| WO | 2012052765 | 4/2012 |

OTHER PUBLICATIONS

Bionic contact lens 'To project emails before eyes,' http://www.kurzweilai.netforums/topic/bionic-contact-lens-to-project-emails-before-eyes, Last accessed Mar. 14, 2012, 2 pages.

Brahim, et al., "Polypyrrole-hydrogel composites for the construction of clinically important biosensors," 2002, Biosensors & Bioelectronics, pp. 53-59, vol. 17.

Chen, et al., "Microfabricated Implantable Parylene-Based Wireless Passive Intraocular Pressure Sensors," Journal of Microelectromechanical Systems, Dec. 2008, pp. 1342-1351, vol. 17, No. 6.

Chu, et al., "Soft Contact-lens Sensor for Monitoring Tear Sugar as Novel Wearable Device of Body Sensor Network," http://www.ksi edu/seke/dms11/DMS/2_Kohji_Mitsubayashi.pdf, Last accessed Jul. 27, 2012, 4 pages.

"Contact Lenses: Look Into My Eyes," The Economist, Jun. 2, 2011 , http://www.econonmist.com/node/18750624/print, Last accessed Mar. 13, 2012, 8 pages.

Haders, "New Controlled Release Technologies Broaden Opportunities for Ophthalmic Therapies," Drug Delivery Technology, Jul./Aug. 2009, pp. 48-53, vol. 8, No. 7.

Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012. 5 pages.

Huang, et al., "Wrinkling of Ultrathin Polymer Films," Mater. Res. Soc. Symp. Proc., 2006, 6 pages, vol. 924, Materials Research Society.

Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.

Liao, et al., "A 3-μW CMOS Glucose Sensor for Wireless Contact-Lens Tear Glucose Monitoring ," IEEE Journal of Solid-State Circuits, Jan. 2012, pp. 335-344, vol. 47, No. 1.

Liao, et al., "A 3-μW Wirelessly Powered CMOS Glucose Sensor for an Active Contact Lens," 2011 IEEE International Solid-State Circuits Conference, Session 2, Feb. 21, 2011, 3 pages.

Lingley, et al., "A Single-Pixel Wireless Contact Lens Display," Journal of Micromechanics and Microengineering, 2011, pp. 1-8.

Lingley, et al., "Multipurpose integrated active contact lenses," SPIE, 2009, 2 pages.

Liu, et al., "Miniature Amperometric Self-Powered Continuous Glucose Sensor with Linear Response," Analytical Chemistry, 2012, 7 pages.

Loncar, et al., "Design and Fabrication of Silicon Photonic Crystal Optical Waveguides," Journal of Lightwave Technology, Oct. 2000, pp. 1402-1411, vol. 18, No. 10.

Murdan, "Electro-responsive drug delivery from hydrogels," Journal of Controlled Release, 2003, pp. 1-17, vol. 92.

Pandey, et al., "A Fully Integrated RF-Powered Contact Lens With a Single Element Display," IEEE Transactions on Biomedical Circuits and Systems. Dec. 2010, pp. 454-461, vol. 4, No. 6.

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.

Selner, et al., "Novel Contact Lens Electrode Array for Multi-electrode Electroretinography (meERG)," IEEE, 2011, 2 pages.

Singh , et al., "Novel Approaches in Formulation and Drug Delivery using Contact Lenses," Journal of Basic and Clinical Pharmacy, May 2011, pp. 87-101, vol. 2, Issue 2.

Thomas, et al., "Functional Contact Lenses for Remote Health Monitoring in Developing Countries," IEEE Global Humanitarian Technology Conference, 2011, pp. 212-217, IEEE Computer Society.

Tweedie, et al., "Contact creep compliance of viscoelastic materials via nanoindentation," J. Mater. Res., Jun. 2006, pp. 1576-1589, vol. 21, No. 2, Materials Research Society.

Wall, K., "Active contact lens that lets you see like the Terminator patented," Feb. 10, 2012, http://vvww.patexia.com/feed/active-contact-lens-that-lets-you-see-like-the-terminator-patented-2407, Last accessed Mar. 28, 2012, 5 pages.

Zarbin, et al., "Nanotechnology in ophthalmology," Can J Ophthalmol, 2010, pp. 457-476, vol. 45, No. 5.

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.

Chu et al., "Biomedical soft contact-lens sensor for in situ ocular biomonitoring of tear contents," Biomed Microdevices, 2011, pp. 603-611, vol. 13.

Chu et al., "Soft contact lens biosensor for in situ monitoring of tear glucose as non-invasive blood sugar assessment," Talanta, 2011, pp. 960-965, vol. 83.

Ho et al., "Contact Lens With Integrated Inorganic Semiconductor Devices," MEMS 2008. IEEE 21st International Conference on. IEEE, 2008., pp. 403-406.

Kudo et al., "A flexible and wearable glucose sensor based on functional polymers with Soft-MEMS techniques," Biosensors and Bioelectronics, 2006, vol. 22, pp. 558-562.

(56) References Cited

OTHER PUBLICATIONS

Lähdesmäki et al., "Possibilities for Continuous Glucose Monitoring by a Functional Contact Lens," IEEE Instrumentation & Measurement Magazine, Jun. 2010, pp. 14-17.

Lingley et al., "A contact lens with integrated micro solar cells," Microsyst Technol, 2012, pp. 453-458, vol. 18.

Parviz, Babak A., "For Your Eyes Only," IEEE Spectrum, Sep. 2009, pp. 36-41.

Patel et al., "Flexible Glucose Sensor Utilizing Multilayer PDMS Process," Engineering in Medicine and Biology Society, 2008. EMBS 2008 30th Annual International Conference on the IEEE, pp. 5749-5752.

Saeedi, E. et al., "Self-assembled crystalline semiconductor optoelectronics on glass and plastic," J. Micromech. Microeng., 2008, pp. 1-7, vol. 18.

Saeedi et al., "Self-Assembled Inorganic Micro-Display on Plastic," Micro Electro Mechanical Systems, 2007. MEMS. IEEE 20th International Conference on. IEEE, 2007., pp. 755-758.

Sensimed Triggerfish, Sensimed Brochure, 2010, 10 pages.

Shih, Yi-Chun et al., "An Inductorless DC-DC Converter for Energy Harvesting With a 1.2-μW Bandgap-Referenced Output Controller," IEEE Transactions on Circuits and Systems-II: Express Briefs, Dec. 2011, pp. 832-836, vol. 58, No. 12.

Shum et al., "Functional modular contact lens," Proc. of SPIE, 2009, pp. 73970K-1 to 73970K-8, vol. 7397.

Stauth et al., "Self-assembled single-crystal silicon circuits on plastic," PNAS, Sep. 19, 2006, pp. 13922-13927, vol. 103, No. 38.

Yao, H. et al., "A contact lens with integrated telecommunication circuit and sensors for wireless and continuous tear glucose monitoring," J. Micromech. Microeng., 2012, pp. 1-10, vol. 22.

Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 μA, Addressable Gent Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

Zhang et al., "Microfabrication and Applications of Opto-Microfluidic Sensors," Sensors, 2011, vol. 11, pp. 5360-5382.

\* cited by examiner

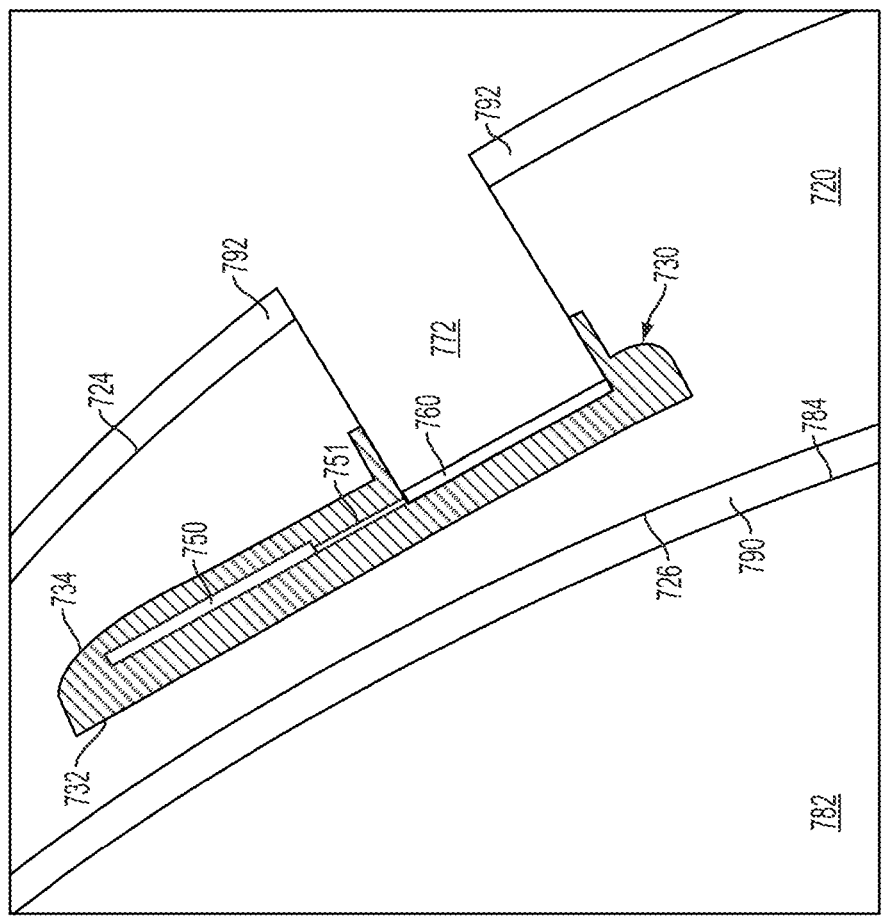
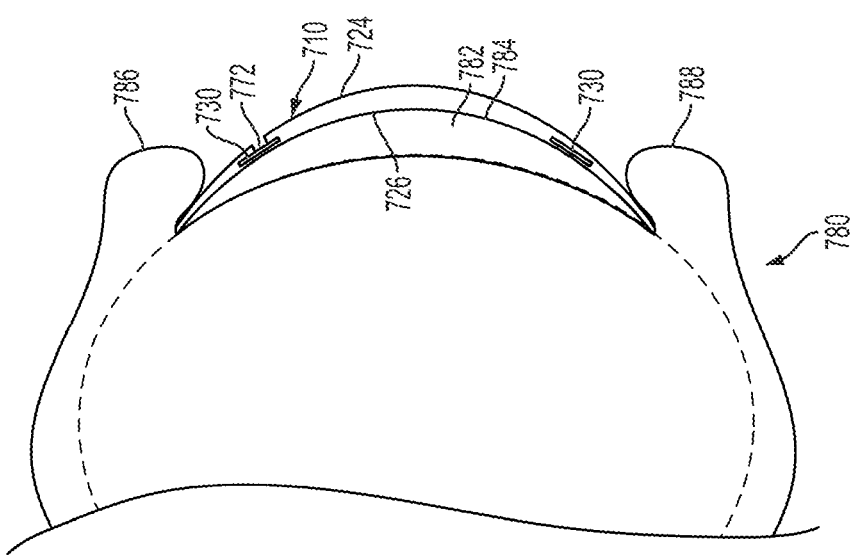

METHODS FOR LEAVING A CHANNEL IN A POLYMER LAYER USING A CROSS-LINKED POLYMER PLUG

BACKGROUND

Unless otherwise indicated herein, the materials described in this section are not prior art to the claims in this application and are not admitted to be prior art by inclusion in this section.

A body-mountable device may be configured to monitor health-related information based on at least one analyte detected in a fluid of a user wearing the body-mountable device. For example, the body-mountable device may comprise an eye-mountable device that may be in the form of a contact lens that includes a sensor configured to detect the at least one analyte (e.g., glucose) in a tear film of a user wearing the eye-mountable device. The body-mountable device may also be configured to monitor various other types of health-related information.

SUMMARY

In one aspect, a method involves: forming a cross-linked polymer plug over a sensor located on a structure, such that the sensor is covered by the cross-linked polymer plug, wherein the sensor is configured to detect an analyte; forming a first polymer layer, wherein the first polymer layer defines a posterior side of an eye-mountable device; positioning the structure on the first polymer layer; forming a second polymer layer over the first polymer layer and the structure to provide a partially-fabricated device in which the structure is fully enclosed by the first polymer layer, the second polymer layer, and the cross-linked polymer plug, wherein the second polymer layer defines an anterior side of the eye-mountable device; and soaking the partially-fabricated device in a fluid, such that the cross-linked polymer plug swells out of the partially-fabricated device to leave a channel in the second polymer layer, wherein the sensor is configured to receive the analyte via the channel.

In another aspect, a device is disclosed. A device includes: a structure including a sensor configured to detect an analyte, wherein the sensor is covered by a cross-linked polymer plug; and a transparent polymer, wherein the structure is fully enclosed by the transparent polymer and the cross-linked polymer plug, and wherein the transparent polymer defines a posterior side and an anterior side of an eye-mountable device.

In yet another aspect, a system is disclosed. A system includes means for forming a cross-linked polymer plug over a sensor located on a structure, such that the sensor is covered by the cross-linked polymer plug, wherein the sensor is configured to detect an analyte; means for forming a first polymer layer, wherein the first polymer layer defines a posterior side of an eye-mountable device; means for positioning the structure on the first polymer layer; means for forming a second polymer layer over the first polymer layer and the structure to provide a partially-fabricated device in which the structure is fully enclosed by the first polymer layer, the second polymer layer, and the cross-linked polymer plug, wherein the second polymer layer defines an anterior side of the eye-mountable device; and means for soaking the partially-fabricated device in a fluid, such that the cross-linked polymer plug swells out of the partially-fabricated device to leave a channel in the second polymer layer, wherein the sensor is configured to receive the analyte via the channel.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 7c is a side cross-section view of the eye-mountable device of FIGS. 7a and 7b while mounted to a corneal surface of an eye, according to an example embodiment.

FIG. 7d is a side cross-section view showing the tear film layers surrounding the surfaces of the eye-mountable device mounted as shown in FIG. 7c, according to an example embodiment.

DETAILED DESCRIPTION

The following detailed description describes various features and functions of the disclosed systems and methods with reference to the accompanying figures. In the figures, similar symbols typically identify similar components, unless context dictates otherwise. The illustrative method and system embodiments described herein are not meant to be limiting. It will be readily understood that certain aspects of the disclosed methods and systems can be arranged and combined in a wide variety of different configurations, all of which are contemplated herein.

I. Introduction

A body-mountable device may be configured to monitor health-related information based on at least one analyte detected in a fluid of a user wearing the body-mountable device. Such a body-mountable device may include a sensor configured to detect the at least one analyte. The sensor can receive the at least one analyte through a channel in a polymer layer of the body-mountable device. When fabricating such a body-mountable device, a partially-fabricated device may be soaked in a fluid, such that a cross-linked polymer plug (e.g., a sacrificial cross-linked polymer plug) formed over the sensor swells out of the partially-fabricated device to leave the channel in the polymer layer. Beneficially, a cross-linked polymer plug may maintain a stable position during formation of a polymer layer, such as a second polymer layer.

As used throughout this disclosure, the anterior side of the eye-mountable device refers to an outward-facing side of the eye-mountable device, whereas the posterior side of the eye-mountable device refers to an inward-facing side of the eye-mountable device. In particular, when the eye-mountable device is mounted on an eye of the user, the anterior side corresponds to a side of the eye-mountable device that is facing outward and thus not touching the eye of the user. Further, when the eye-mountable device is mounted on an eye of the user, the posterior side corresponds to a side of the eye-mountable device that is facing inward and thus touching the eye of the user.

II. Example Methods

Figure 1:
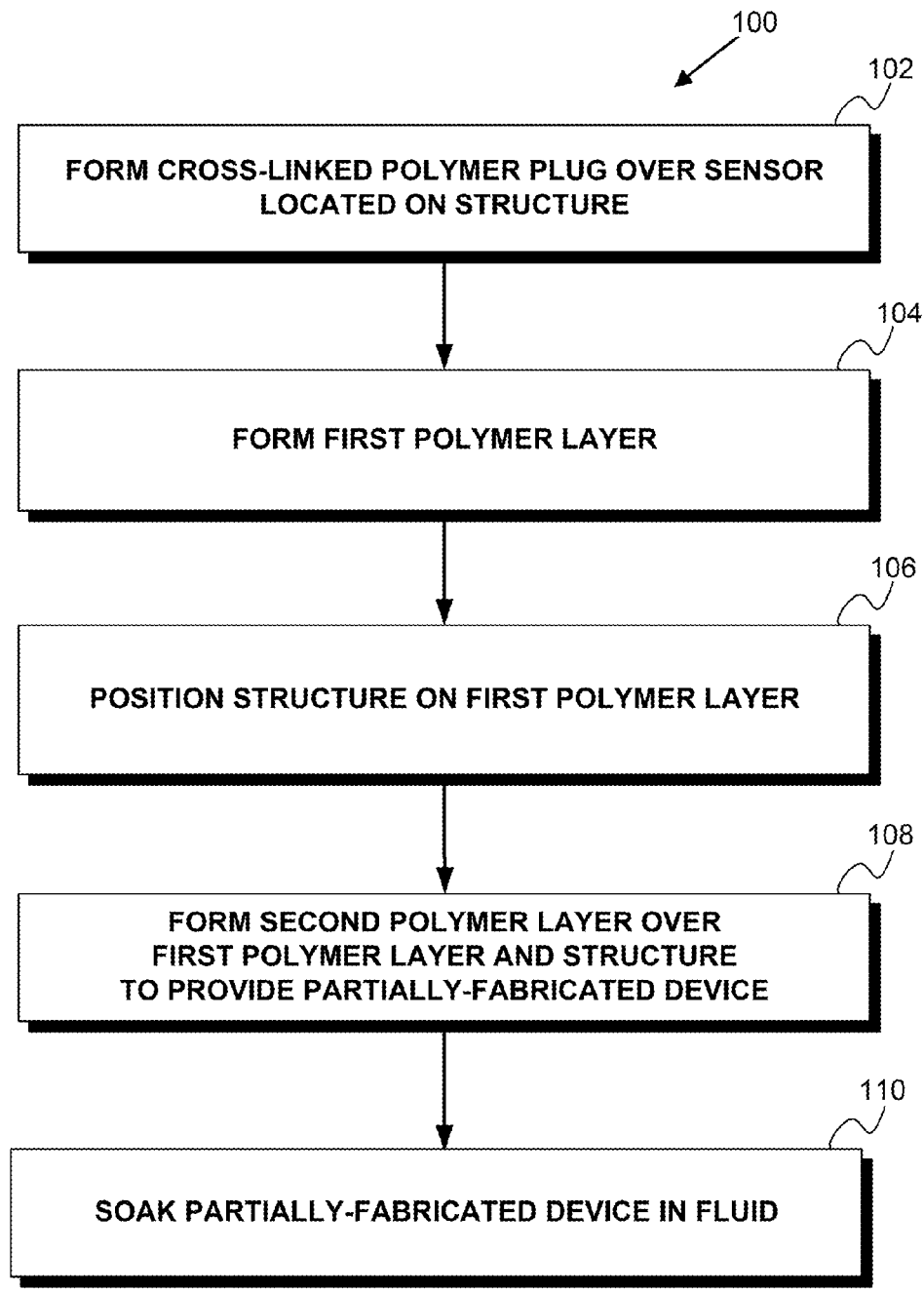
FIG. 1 is a flow chart illustrating a method according to an example embodiment.

Example methods for fabricating a body-mountable device are disclosed. FIG. 1 is a flow chart illustrating a method 100 according to an example embodiment. More specifically, the method 100 involves forming a cross-linked polymer plug over a sensor located on a structure, such that the sensor is covered by the cross-linked polymer plug, as shown by block 102. The method 100 may then involve forming a first polymer layer, as shown by block 104. Further, the method 100 may then involve positioning the structure on the first polymer layer, as shown by block 106. Further still, the method 100 may then involve forming a second polymer layer over the first polymer layer and the structure to provide a partially-fabricated device in which the structure is fully enclosed by the first polymer layer, the second polymer layer, and the cross-linked polymer plug, as shown by block 108. The method 100 may then involve soaking the partially-fabricated device in a fluid, such that the cross-linked polymer plug swells out of the partially-fabricated device to leave a channel in the second polymer layer, as shown in block 110.

For purposes of illustration, the method 100 is described below as being carried out by a fabrication device that utilizes cast or compression molding, among other processes. It should be understood, however, that the method 100 may be carried out by a fabrication device that utilizes other methods and/or processes for forming body-mountable devices.

Moreover, for purposes of illustration, the method 100 is described below in a scenario where a body-mountable device comprises an eye-mountable device. It should be understood, however, that the method 100 may involve scenarios where the body-mountable device comprises other mountable devices that are mounted on or in other portions of the human body. For example, the method 100 may involve a scenario where the body-mountable device comprises a tooth-mountable device and/or a skin mountable device as described herein.

A. Forming a Cross-Linked Polymer Plug Over a Sensor Located on a Structure

Figure 2A:
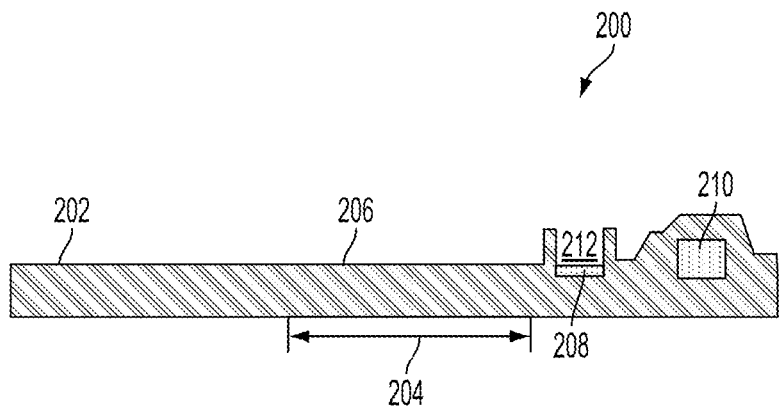
FIG. 2a is an illustration of formation of a cross-linked polymer plug over a sensor located on a structure, according to an example embodiment.
Figure 2B:
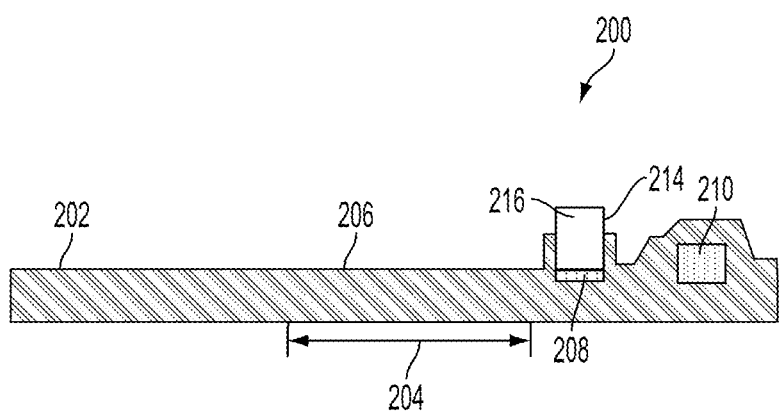
FIG. 2b is an illustration of a cross-linked polymer plug formed over a sensor located on a structure, according to an example embodiment.

As mentioned above, at block 102, the fabrication device may be used to form a cross-linked polymer plug over a sensor located on a structure, such that the sensor is covered by the cross-linked polymer plug. Beneficially, the cross-linked polymer plug can maintain a stable position during subsequent formation steps, such as formation of a second polymer layer. FIGS. 2*a* and 2*b* illustrate a fabrication device 200 that includes example equipment for forming a cross-linked polymer plug 214 over a sensor 208 located on a structure 202.

In an example, the structure 202 has an outer diameter and a hole 204 that defines an inner diameter. And the structure 202 includes a polymer 206, the sensor 208, and electronics 210. The structure 202 may occupy a peripheral portion of an eye-mountable device, such as an eye-mountable device 300 illustrated in FIG. 3, so as to limit interference with a user's field of view when the eye-mountable device is mounted on an eye of the user. The polymer 206 may comprise a variety of polymeric materials, such as paralyene.

In the illustrated example, the electronics 210 is embedded in the polymer 206, and the sensor 208 is surrounded by the polymer 206, except for the sensor 208 being exposed by an opening 212. However, in other examples, the sensor 208 and electronics 210 may be mounted on a top surface of the polymer 206. With this arrangement, the structure 202 might not include the opening 212. In some embodiments, the opening 212 can have a dimension of between 500 to 700 micrometers. Other dimensions are possible as well. And, in some embodiments, the opening 212 can have a square shape with rounded corners. Other shapes are possible as well, such as rectangular, circular, etc.

The structure 202 can have various sizes. For instance, the size of the structure 202 may depend on which analyte (or analytes) an eye-mountable device is configured to detect. In an example, the structure 202 is a substrate shaped as a ring with approximately a 1 centimeter diameter, a radial thickness of approximately 1 millimeter, and a maximum height of approximately 50 between 150 micrometers. Of course, other sizes of the structure 202 are possible as well.

In an example, the structure 202 has a height dimension of at least 50 micrometers. In other words, at some point of the structure 202, the height of the structure 202 may be at least 50 micrometers. In such an example, this height dimension may correspond to a maximum height of the structure 202. In accordance with the present disclosure, the maximum height of the structure 202 corresponds to the height of the structure 202 at its highest point. For instance, in the example where the structure 202 comprises the sensor 208 and the electronics 210, the height of the structure 202 may vary (and thus the structure 202 may have various height dimensions). For example, the height of the structure 202 may be higher at a point where the electronics 210 is mounted on the structure 202, whereas the height may be lower at a point where there is no chip on the structure 202. In such an example, the maximum height may correspond to the point where the electronics 210 is located on the structure 202.

The sensor 208 can be configured in a variety of ways. As one example, the sensor 208 may comprise a pair of electrodes, such as a working electrode and a reference electrode, configured to detect one or more analytes. Other configurations of the sensor 208 are possible as well. And the sensor 208 can have a variety of thicknesses. As one example, the sensor 208 can have a thickness of 260 nanometers. Other thicknesses of the sensor 208 are possible as well.

The electronics 210 can be configured in a variety of ways. As one example, the electronics 210 can comprise a chip including one or more logic elements configured to operate the sensor 208. Other configurations of the electronics 210 are possible as well.

In an example, forming the cross-linked polymer plug 214 over the sensor 208 located on the structure 202 can include injecting a polymerizable mixture 216 over the sensor 208 and curing the polymerizable mixture 216. With this arrangement, the fabrication device 200 may be configured to inject the polymerizable mixture 216 over the sensor 208. In some embodiments, the fabrication device 200 can inject the polymerizable mixture 216 into the opening 212. With this approach, the cross-linked polymer plug 214 might take the shape of or be similar in shape to the opening 212. Moreover, in some embodiments, the polymerizable mixture 216 can be injected into the opening 212, such that a portion of the polymerizable mixture 216 is located over the opening 212. With this approach, the maximum height of the structure 202 may correspond to the point where the cross-linked polymer plug 214 is located on the structure 202.

In some embodiments, the fabrication device 200 may include an injector, such as a microcapillary injector, that injects the polymerizable mixture 216 over the sensor 208. With this approach, the injector can inject a predetermined quantity of the polymerizable mixture 216 over the sensor 208 before subsequent formation steps, such as cross-linking with heat or light. And in such embodiments, the injector may be Nanoject™ sold by Debiotech.

Curing involves initiating the polymerization reaction of the monomers and/or macromonomers in the polymerizable mixture 216, and results in the formation of the cross-linked polymer plug 214. Curing may be, for example, brought about by chemical additives, ultraviolet radiation, electron beam, and/or heat. In some embodiments, the polymerizable mixture 216 can be a light-curable, and the fabrication device 200 may be configured to cure the light-curable polymerizable mixture using light, such as ultraviolet light or visible light. The fabrication device 200 may be configured to cure different polymerizable mixtures differently than other polymerizable mixtures (e.g., a first polymerizable mixture may be cured more than a second polymerizable mixture). Further, in addition to light curing, other methods of curing are possible as well, such as chemical additives and/or heat.

In another example, forming the cross-linked polymer plug 214 over the sensor 208 located on the structure 202 can include spin coating the polymerizable mixture 216 over the sensor 208 and photopatterning the polymerizable mixture 216. With this arrangement, the fabrication device may be configured to spin coat the polymerizable mixture 216 over the sensor 208. In some embodiments, the fabrication device 200 can spin coat the polymerizable mixture 216 into the opening 212. With this approach, the cross-linked polymer plug 214 might take the shape of or be similar in shape to the opening 212. Moreover, in some embodiments, the polymerizable mixture 216 can be spin coated into the opening 212, such that a portion of the polymerizable mixture 216 is located over the opening 212. With this approach, the maximum height of the structure 202 may correspond to the point where the cross-linked polymer plug 214 is located on the structure 202.

In some embodiments, the fabrication device 200 may include a spin coating machine, such as a spin coater (e.g., ACE-1020 Series), that spin coats the polymerizable mixture 216 over the sensor 208.

Moreover, in some embodiments, the fabrication device 200 may be configured to photopattern the polymerizable mixture 216.

The cross-linked polymer plug 214 could take various different forms in various different embodiments. For instance, in some embodiments, the cross-linked polymer plug 214 includes a cross-linked polymer capable of increasing in volume when contacted with a fluid. In some instances, the cross-linked polymer plug 214 can be a hydrophilic polymer that swells upon contact with an aqueous solution, such as a hydrogel. In some embodiments, the cross-linked polymer plug 214 can be compliant, such that the cross-linked polymer plug 214 may deform during subsequent formation steps, such as formation of a second polymer layer. In other instances, the cross-linked polymer plug 214 can be formulated for specific properties, such as, maintaining form during the formation of one or more polymer layers, such as a first or second polymer layer. Polymer properties can also be chosen for compatibility with one or more fluids used in formation steps, such as swelling when treated with a fluid used in a soaking step.

In some embodiments, the cross-linked polymer plug 214 includes:
  backbone chains having
    first methacrylate-derived units, each having a side chain; and
    second methacrylate-derived units; and
  crosslinks between second methacrylate-derived units in different backbone chains.

In some embodiments, the side chain of the first methacrylate-derived monomers can be chosen from a variety of moieties. In some instances, the side chain can be covalently bound through the carboxylate of the methacrylate monomeric unit, optionally through a linker. The crosslinks, or groups through which the second methacrylate-derived units of different backbone chains are connected to each other, are discussed in greater detail below.

In other embodiments, the backbone chains of the cross-linked polymer plug 214 include one or more additional first methacrylate-derived units, each having a side chain. In some instances, the side chain of the additional units are different than the side chains of the first methacrylate-derived monomeric units, providing a crosslinked copolymer plug.

In some embodiments, the backbone chains of the cross-linked polymer plug 214 include methacrylate-derived monomeric units derived from a methacrylated polymer (i.e., a "methacrylate macromonomer"). One of ordinary skill in the art will recognize methacrylate macromonomers as being derived from the reaction of a polymer having one or more reactive groups, with a methacrylate monomer having one or more complimentarily reactive groups (i.e., a methacrylation agent). In some instances the polymer can have nucleophilic groups, such as hydroxyl, carboxylate, amino or thiol groups, and the methacrylation agent can have an electrophilic group, for example, an ester, isocyanate or an epoxide. In other instances, the methacrylation agent can be nucleophilic, and the polymer can have an electrophilic group. Examples of methacrylate macromonomers include, but are not limited to, methacrylated poly(vinylpyridine), methacrylated poly(allylamine), methacrylated chitosan and methacrylated hyaluronic acid. The units derived from methacrylated macromonomers will herein be referred to as "methacrylate-derived macromonmeric units".

One of ordinary skill in the art will recognize that methacrylated macromonomers have multiple methacrylate groups that can polymerize upon curing of the polymerizable mixture 216. The presence of one or more methacrylated macromonomers in the polymerizable mixture 216 can provide a cross-linked polymer plug 214 in which one or more backbone chains are connected through a macromonomer side chain as well as through the crosslinks between second methacrylate-derived units in different backbone chains.

In some embodiments, the cross-linked polymer plug 214 includes methacrylate monomeric units covalently bound to side chains include one or more alkylene oxide units. The alkylene oxide units can be derived from ethylene oxide, propylene oxide or butylene oxide, and can be a combination of two or three different alkylene oxide units. In some embodiments, the alkene oxide units form a poly(alkylene oxide) such as poly(ethylene glycol) or polypropylene glycol).

For example, the cross-linked polymer plug 214 can include first methacrylate-derived monomeric units having the formula (I):

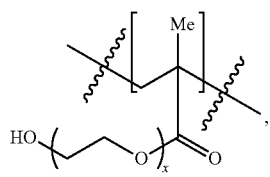
(I)

wherein x is such that the number average molecular weight ($M_n$) of the corresponding monomeric unit is about 100 to about 10,000. In some embodiments, x can be an average number from about 1 to about 250.

In some embodiments, the cross-linked polymer plug 214 includes methacrylate monomeric units covalently bound to a side chain containing one or more nitrogen moieties. For example, the nitrogen moiety can be part of a heterocycle, heteroaromatic, mono-, di-, and tri-alkyl amine, allyl amine, benzyl amine, amino saccharide, amino polysaccharide, and derivatives thereof.

For example, the cross-linked polymer plug 214 can includes monomeric units having the formula (II):

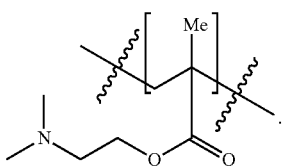
(II)

In some embodiments, the cross-linked polymer plug 214 can include methacrylate monomeric units covalently bound to a side chain having a carboxylic acid group. In some instances, the cross-linked polymer plug 214 includes monomeric units having the formula (III):

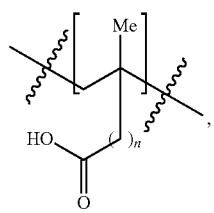
(III)

where n can be 0, 1, 2, 3, 4, 5, 6, 7, 8, 9 or 10.

In other embodiments, the cross-linked polymer plug 214 includes methacrylate-derived macromonomeric units having the formula (IV):

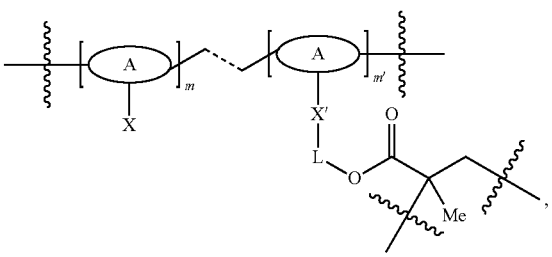
(IV)

where A is a repeating unit monomeric unit, X is a reactive group, X' is X with a positive charge or one less hydrogen atom, L is a linker, and the ratio of m:m' is about 2:1 to about 50:1. In certain embodiments, the ratio is about 5:1 to about 15:1, and in some instances, about 9:1. "A" can be selected from a variety of monomeric units, such as saccharides and ethylenically unsaturated units, including, but not limited to acryl-, methacryl, ethacryl, itaconyl, styryl, acrylamidyl, methacrylamidyl, vinyl and allyl units.

In some embodiments, the reactive group (X), includes a nucleophilic moiety, such as a hydroxyl, amino or thiol group. Amino groups can include primary, secondary and tertiary amines, and nitrogen-containing heterocycles.

It will be recognized by one of ordinary skill in the art that only a portion of the reactive groups on the polymer will form a covalent bond to the methacrylation agent, and the ratio of m:m' can be controlled by the relative stoichiometries of the polyer:methacrylation agent used in the synthesis of the methacrylate macromonomer. It will also be recognized that when the atom of group X that forms a covalent bond with the methacrylation agent has a hydrogen atom, it may lose a hydrogen atom (X'). When the atom of group X that forms a covalent bond with the methacrylation agent lacks a hydrogen atom, X' may have a positive charge.

For example, in some embodiments, the methacrylate-derived macromonomeric units can be derived from allylamine and have the formula (IVa):

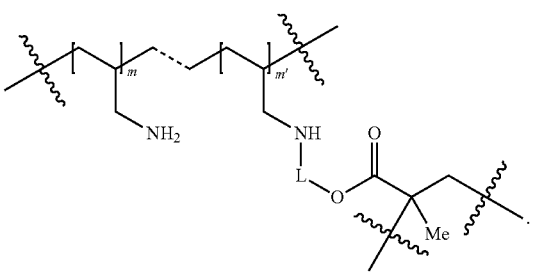
(IVa)

In other embodiments, the methacrylate-derived macromonomeric units can be derived from vinylpyridine and have the formula (IVb):

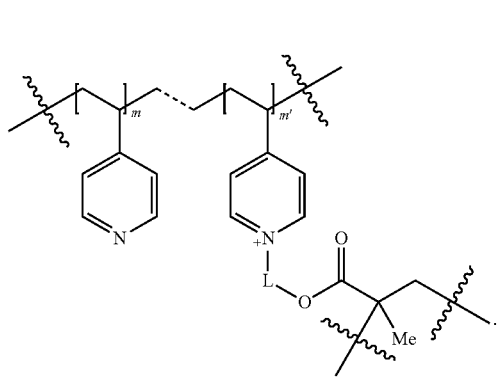

(IVb)

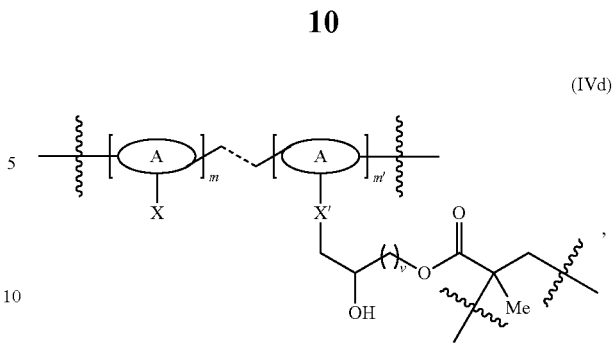

(IVd)

where v is 1, 2, 3, 4, 5, 6, 7, 8, 9 or 10.

In some embodiments, the L is derived from a group having one or more isocyanate moieties. Chemical reaction of the isocyanate with the reactive groups of a polymer can provide an L group having or more urea moieties. In such embodiments, the first methacrylate-derived units can have the structure of formula (IVe):

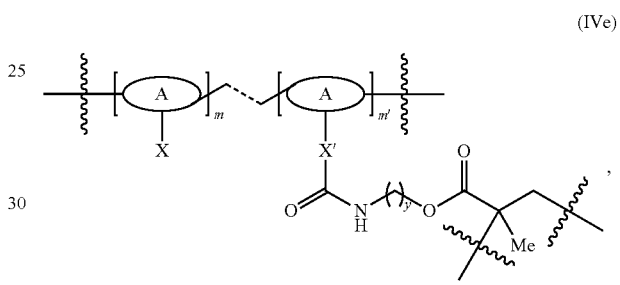

(IVe)

In some embodiments, the reactive group (X), includes an electrophilic moiety, such as an ester, isocyanate or an epoxide, and undergoes methacrylation with a methacrylation agent having one or more nucleophilic moieties. Nucleophilic moieties include hydroxyl, amino and thiol groups. Amino groups can include primary, secondary and tertiary amines, and nitrogen-containing heterocycles.

In other embodiments, the cross-linked polymer plug 214 includes macromonomeric units derived from methacrylated polysaccharides. The polysaccharides can have the general formula of $C_x(H_2O)_y$, where x can be between about 200 and about 2500. The polysaccharides can also include glycosaminoglycans and polysaccharides modified to contain one or more thiol moieties. For example, the cross-linked polymer plug 214 can having the formula (IVc):

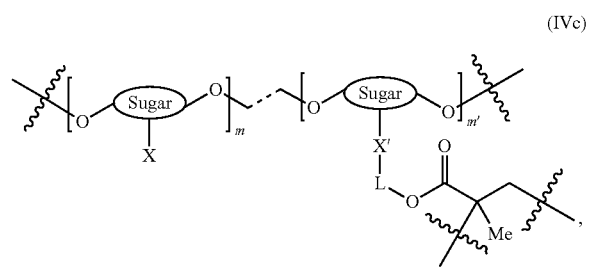

(IVc)

where y is 1, 2, 3, 4, 5, 6, 7, 8, 9 or 10.

In some instances the methacrylation agent can be 2-isocyanatoethyl methacrylate or glycidyl methacrylate.

The crosslinks of cross-linked polymer plug 214 are groups through which the second methacrylate-derived units of different backbone chains are connected to each other, and are represented by "W" in formula (V):

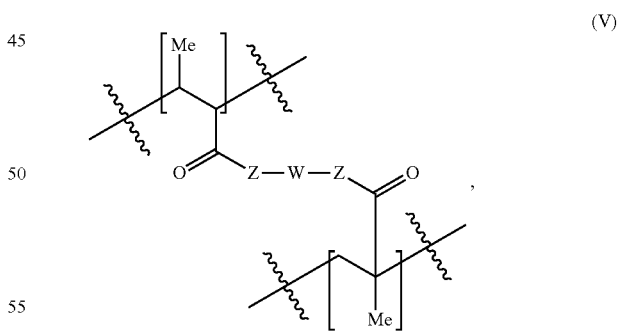

(V)

where the sugar unit is a saccharide unit, and X, X', L, and the ratio of m:m' are as described herein. In some instances, the polysaccharide is chitosan or hyaluronic acid. L is a linker that can be derived from any group capable of undergoing chemical reaction with one or more reactive groups (X) of a polymer to form a covalent bond. The linker can be derived from a group having a nucleophilic or electrophilic moiety, such as hydroxyl, thiol and amino groups, carboxylate, epoxide or isocyanate groups.

In some embodiments, the L is derived from a group having one or more epoxide moieties. Chemical reaction of the epoxide with the reactive groups of a polymer can proceed through nucleophilic attack of the polymer at the electrophilic epoxide carbon atom, providing a L group having or more secondary alcohol moieties. In such embodiments, the first methacrylate-derived units can have the structure of formula (IVd):

where Z is independently —O—, —NR'— or —S—, and W is a hydrophilic group.

In some embodiments, the crosslinks are hydrophilic. The crosslinks can be soluble in water or a water-miscible solvent, such as an alcohol. The crosslinks can have one or more heteroatoms, for example, nitrogen, oxygen or sulfur atoms. In some embodiments, the crosslinks have one or more hydroxy groups.

In some embodiments, the crosslinks include one or more alkylene oxide units. The alkylene oxide units can be in the form of a polymer, such as poly(ethylene glycol), poly(propylene glycol), poly(butylene oxide) or a mixture thereof, and can be a copolymer including a combination of two or three different alkylene oxide units. In some embodiments, the poly(alkylene oxide) of the crosslinks is a block copolymer including blocks of two or three different poly(alkylene oxide) polymers. In certain embodiments, the poly(alkylene oxide) is a block copolymer of poly(ethylene glycol) and poly(propylene glycol). In other embodiments, the crosslinks include poly(ethylene glycol) (PEG).

In some embodiments, the crosslinks include one or more ethylene oxide units. For example, the crosslinks (e.g., A in formula (V) above) can have the structure of formula (Va):

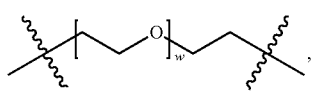

(Va)

where w is 0, 1, 2, 3, 4, 5, 6, 7, 8, 9 or 10.

In certain embodiments, w is an average value of from about 2 to about 250.

In other embodiments, w in the crosslinks of formula (Va) is such that the number average molecular weight ($M_n$) of the PEG portion (within the brackets in formula (Va)) of the crosslinks is about 100 to about 10,000. For example, w can be selected such that the $M_n$ of the PEG portion of the crosslinks falls within a range in Table 1:

TABLE 1

| $M_n$ range of the PEG portion of the crosslinks (values are approximate). | |
|---|---|
| Low | High |
| 100 | 200 |
| 200 | 300 |
| 300 | 400 |
| 400 | 500 |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In some embodiments, the crosslinks are derived from di(ethylene glycol) dimethacrylate, i.e., compounds of formula (V) or (Va) where Z is —O— and w is 1.

In some embodiments, the side chain of the cross-linked polymer plug 214 can be formulated so that the plug does not swell during the formation of one or more polymer layers, such as a first or second polymer layer. For instance, when the formation of the first or second polymer layer includes the use of basic conditions (pH greater than 7), a cross-linked polymer plug 214 comprising poly(ethylene glycol) side chains may swell prematurely. In such a situation, a cross-linked polymer plug 214 comprising nitrogen-containing side chains can be used. The basicity of the nitrogen moieties will resist water absorption (and thus swelling) under basic conditions. The cross-linked polymer plug 214 can then be treated under acidic conditions (pH less than 7) to induce swelling when desired.

Alternatively, when the manufacture of one or more polymer layers requires a cross-linked polymer plug 214 that is resistant to water absorption under acidic conditions (pH less than 7), a cross-linked polymer plug 214 comprising carboxylic acid groups can be used. The acidity of the carboxylic acid group will resist water absorption under acidic conditions, but will swell when treated under basic conditions (pH greater than 7).

Moreover, the cross-linked polymer plug 214 can have a variety of thicknesses. As one example, the cross-linked polymer plug 214 can have a thickness of up to 100 micrometers. Other thicknesses are possible as well. In the illustrated example, when the cross-linked polymer plug 214 is formed over the sensor 208, the cross-linked polymer plug 214 may have a height dimension that is greater than the height dimension of the electronics 210 located on the structure 202.

The formation of the cross-linked polymer plug 214 includes depositing the precursors of the cross-linked polymer (polymerizable mixture 216) on the sensor 208, and initiating polymerization (curing) so that the sensor 208 is covered by the resulting cross-linked polymer plug 214.

In some embodiments, the formation of the cross-linked polymer plug 214 includes:

a) depositing a polymerizable mixture including one or more methacrylate monomers, a crosslinking agent, and an initiator onto the surface of the sensor 208; and b) curing the deposited polymerizable mixture.

The polymerizable mixture can be formed in an aqueous medium, alcoholic medium, or mixture thereof. The aqueous medium can include a buffered aqueous solution, such as, for example, a solution containing citric acid, acetic acid, borate, carbonate, bicarbonate, 4-2-hydroxyethyl-1-piperazineethanesulfonic acid (HEPES), 3-{[tris(hydroxymethyl)methyl]amino}propanesulfonic acid (TAPS), N,N-bis(2-hydroxyethyl)glycine (Bicine), tris(hydroxymethyl)methylamine (Tris), N-tris(hydroxymethyl)methylglycine (Tricine), 3-[N-Tris(hydroxymethyl)methylamino]-2-hydroxypropanesulfonic Acid (TAPSO), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate), saline sodium citrate (SSC), 2-(N-morpholino) ethanesulfonic acid (MES), 2(R)-2-(methylamino)succinic acid, or phosphate buffered saline (PBS). In some embodiments, the polymerizable mixture is formed in a mixture of a buffered aqueous solution and ethanol.

The methacrylate monomer are selected to provide the first methacrylate-derived monomeric units of the cross-linked polymer plug 214. In some embodiments, the methacrylate monomer has a side chain that includes one or more alkylene oxide units. In some instances, the monomer can have the formula (VI):

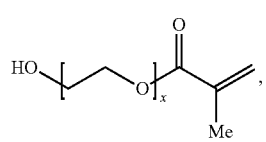

(VI)

where x is selected to provide the first methacrylate-derived monomeric unit of the cross-linked polymer plug 214, as described herein.

In other embodiments, the cross-linked polymer plug 214 can be formed with one or more monomers suitable for the resulting cross-linked polymer plug 214 to be a hydrogel.

In some embodiments, the formation of the cross-linked polymer plug 214 includes a monomer covalently bound to a side chain containing one or more nitrogen moieties. For example, the nitrogen moiety can be part of a heterocycle, heteroaromatic, mono-, di-, and tri-alkyl amine, allylamine, benzylamine, amino saccharide, amino polysaccharide, and derivatives thereof. For example, in some embodiments, the monomer can have the formula (VII):

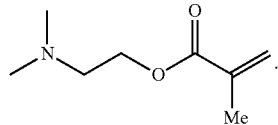

(VII)

In some embodiments, the methacrylate monomer includes a side chain having a carboxylic acid group. For example, the monomer can have the formula (VIII):

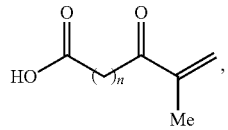

(VIII)

where n is selected to provide the first methacrylate-derived monomeric unit of the cross-linked polymer plug 214, as described herein.

In some embodiments, methacrylate monomer is a methacrylate macromonomer derived from the methacrylation of a polymer such as poly(vinyl amine), poly(vinyl pyridine), chitosan or hyaluronic acid. For example, the methacrylate monomer can be a methacrylate macromonomer having the formula (IX):

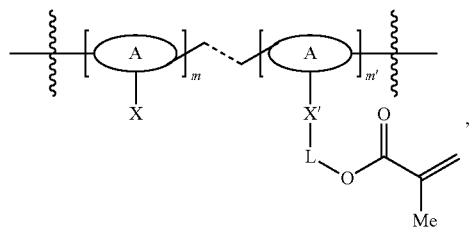

(IX)

where A, X, X', L, m and m' are selected to provide the first methacrylate-derived monomeric unit of the cross-linked polymer plug 214, as described herein.

In some embodiments, the methacrylate macromonomer has the formula (IXa):

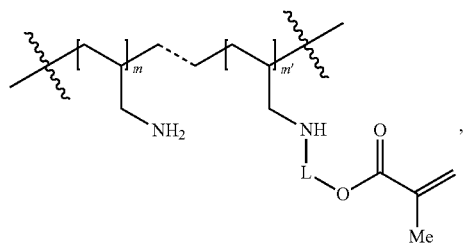

(IVa)

where L, m and m' are selected to provide the first methacrylate-derived monomeric unit of the cross-linked polymer plug 214, as described herein.

In some embodiments, the methacrylate macromonomer has the formula (IXb):

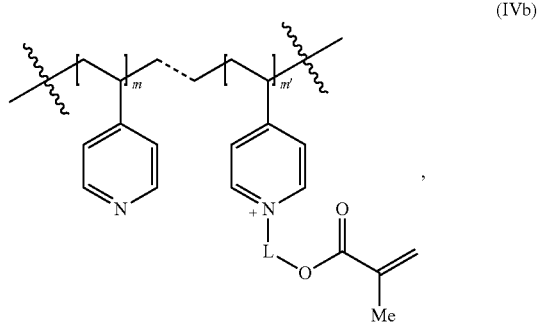

(IVb)

where L, m and m' are selected to provide the first methacrylate-derived monomeric unit of the cross-linked polymer plug 214, as described herein.

In some embodiments, the methacrylate macromonomer has the formula (IXc):

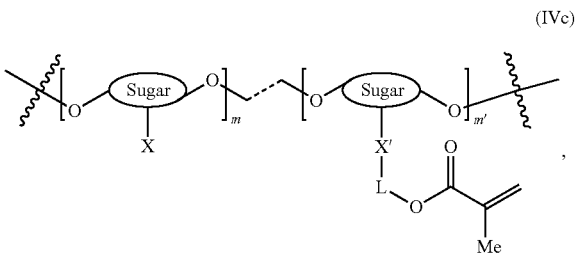

(IVc)

where the sugar unit, X, X', L, m and m' are selected to provide the first methacrylate-derived monomeric unit of the cross-linked polymer plug 214, as described herein.

In some embodiments, the methacrylate macromonomer has the formula (IXd):

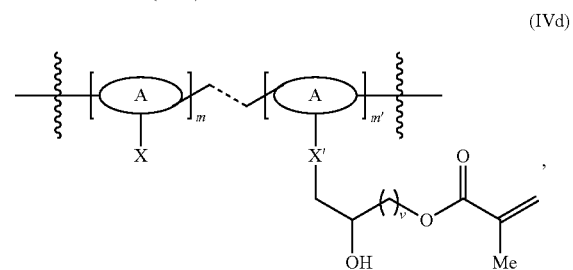

(IVd)

where A, X, X', v, m and m' are selected to provide the first methacrylate-derived monomeric unit of the cross-linked polymer plug 214, as described herein.

In some embodiments, the methacrylate macromonomer has the formula (IXe):

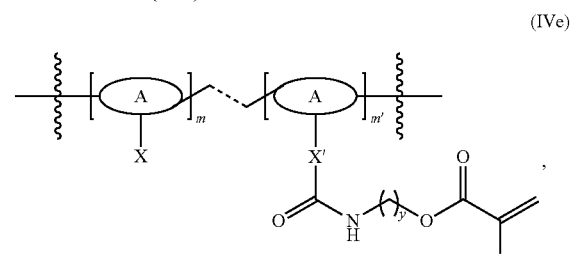

(IVe)

where A, X, X', y, m and m' are selected to provide the first methacrylate-derived monomeric unit of the cross-linked polymer plug 214, as described herein.

In some embodiments, the polymerizable mixture 216 includes more than one methacrylate monomer, where each monomer has a different side chain. The depositing and curing of the polymerizable mixture 216 can provide a cross-linked copolymer plug that is a copolymer having methacrylate backbone chains with two or more different side chains.

The crosslinking agent is a dimethacrylate monomer having two terminal methacrylate groups tethered by a hydrophilic linker. The hydrophilic linker is selected to provide the crosslinks between the second methacrylate-derived units in different backbone chains of the cross-linked polymer plug 214, as described herein.

In some embodiments, the hydrophilic linker of the crosslinking agent includes one or more alkylene oxide units. The alkylene oxide units can be in the form of a polymer, such as poly(ethylene glycol), polypropylene glycol), poly(butylene oxide) or a mixture thereof, and can be a copolymer including a combination of two or three different alkylene oxide units. For example, in some embodiments, the crosslinking agent can have the formula (X):

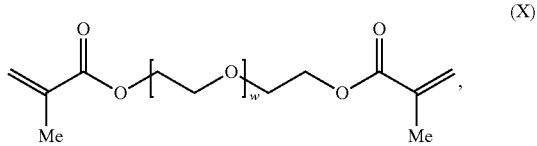

(X)

where w is selected to provide the crosslinks of the cross-linked polymer plug 214, as described herein.

The method of curing (i.e., initiating polymerization) the polymerizable mixture 216 can be dictated by the initiator used, which can be chosen for the desired initiation efficiency and/or initiation conditions. Initiators can be activated by a wide range of physical and chemical conditions, such as thermal decomposition, photolysis, redox reactions, persulfates, ionizing radiation, electrolysis and sonication. In some examples, the polymerizable mixture 216 can be cured with ultraviolet (UV) light. In some embodiments, the polymerizable mixture 216 can be spin-coated onto the sensor. In some embodiments, the polymerizable mixture 216 can be photo-patterned on the sensor.

In one example, cross-linked polymer plug 214 is formed by spin-coating a 17:1:1:1 mixture of PEG950MA (polyethylene glycol methacrylate with an Mn of 950), PEG600DMA (polyethylene glycol dimethacrylate with an Mn of 600), Darucur 1173 (initiator) and Red Dye onto a silicon wafer and radiating the area over the sensor 208. The unpolymerized PEG residue rinsed away from the rest of the wafer.

In another example, a 30% solution of Poly(4-vinyl pyridine) [mol. wt. 160K] functionalized with methacrylate groups in EtOH containing 1 wt % Darocur 1173 is spun on a silicone wafer and the area over the sensor is irradiated. The non-polymerized formulation is rinsed from the wafer after photopolymerization.

Although the polymeric plugs in the above examples comprise methacrylate groups, there are a number of ethylenically unsaturated groups known in the art to be capable of undergoing polymerization. Ethylenically unsaturated monomers and macromonomers may be either acrylic- or vinyl-containing. Vinyl-containing monomers contain the vinyl grouping ($CH_2$=CH—), and are generally highly reactive. Acrylic-containing monomers are represented by the formula:

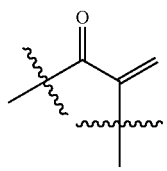 [SMILES: *C(=C)C(*)=O]

Examples of suitable polymerizable groups may include acrylic-, ethacrylic-, itaconic-, styryl-, acrylamido-, methacrylamido- and vinyl-containing groups such as the allyl group.

In addition to the above disclosed methods of forming crosslinked polymeric networks by the polymerization of ethylenically unsaturated monomers and macromonomers, additional chemistries will be known to one of ordinary skill in the art to from such networks. As an example, epoxy chemistry, in which multifunctional amines and multifunctional epoxy compounds are mixed together and cured, can be used to form cross-linked polymer networks. Additionally, urethane chemistry may be used, in which multifunctional isocyanates are mixed with multifunctional alcohols and cured to provide cross-linked polymer networks. Other chemistries for the formation of cross-linked polymer networks exist, and will be well known to those of ordinary skill in the art.

B. Forming a First Polymer Layer

Figure 2C:
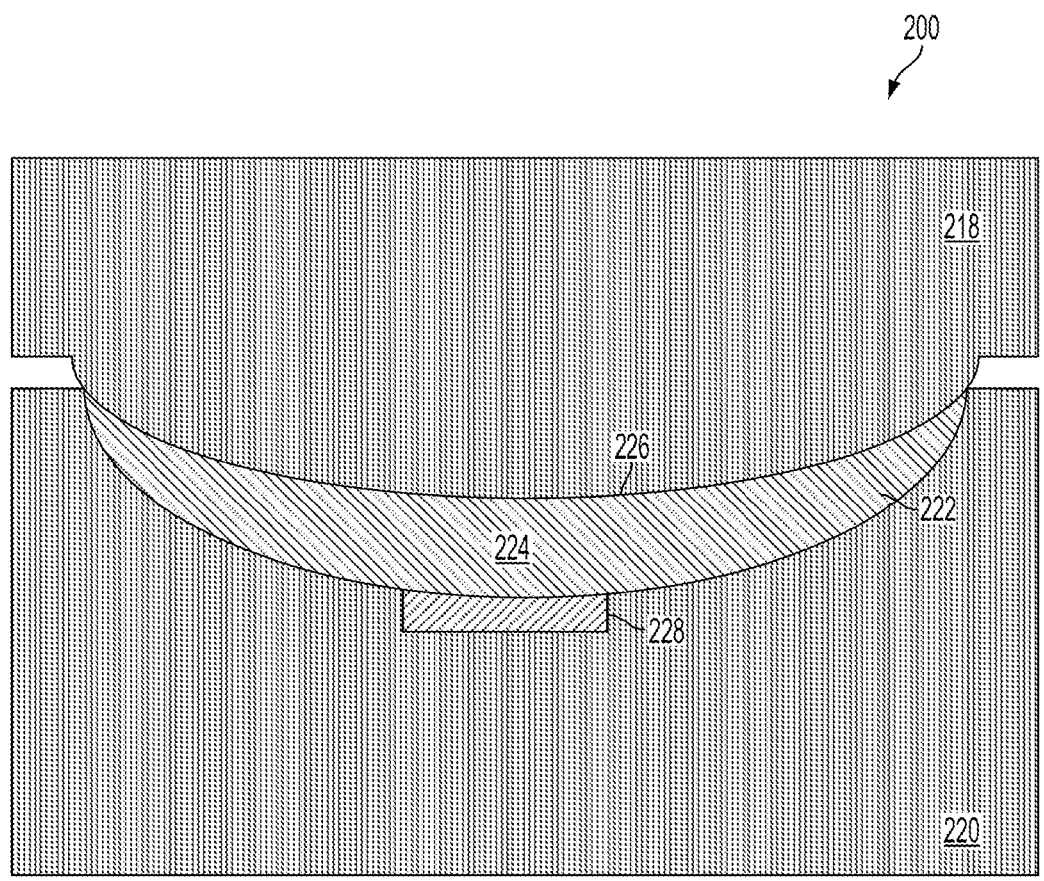
FIG. 2c is an illustration of formation of a first polymer layer, according to an example embodiment.

As mentioned above, at block 104, the fabrication device may be used to form a first polymer layer. The fabrication device may include molding pieces, such as molding pieces that are suitable for cast molding. FIG. 2c illustrates the fabrication device 200 includes molding pieces that may be used to form the first polymer layer. In particular, FIG. 2c illustrates the fabrication device 200 including a first molding piece 218 and a second molding piece 220. The first molding piece 218 and the second molding piece 220 may define a first cavity. The second molding piece 220 may be filled with a polymer material 222, and the polymer material 222 may be compressed into a first polymer layer 224 by the first molding piece 218.

After the polymer material 222 is compressed into the first polymer layer 224, the fabrication device 200 may cure the first polymer layer 224. In an example, the polymer material 222 can be a light-curable polymer material, and the fabrication device 200 may be configured to cure the light-curable polymer material using light, such as ultraviolet light or visible light. In an example, the first polymer layer 224 may be cured to a partially-cured state. In such an example, this may involve curing the material to a partially-cured state that is approximately 50-75% of a fully cured state. Other partially-cured states are possible as well. Beneficially, by partially curing the first polymer layer to a partially-cured state, the first polymer layer 224 may have a tackiness that facilitates adhesion thereto. With this arrangement, the tackiness may ensure that a structure placed on the first polymer layer 224 remains securely fixed in a given location during subsequent formation steps.

The tackiness exhibited by the partially-cured first polymer layer 224 may be different for different polymers. Accordingly, the fabrication device 200 may be configured to cure different polymer materials differently than other polymer materials (e.g., a first polymer material may be cured more than a second polymer material). Further, in addition to light curing, other methods of curing are possible as well, such as chemical additives and/or heat. Yet still further, in other example embodiments, the first polymer layer 224 may be completely cured. Alternatively, the fabrication device 200 may bypass curing the first polymer layer 224 at this stage.

The first molding piece 218 and the second molding piece 220 may be configured to achieve a given desired thickness of the first polymer layer 224. For instance, in an example, the first polymer layer 224 can have a thickness of less than 150 micrometers. In an example embodiment, the first molding piece 218 and the second molding piece 220 can be designed so as to allow for a layer having less than a 150 micrometer thickness between the two cavities. As such, when the first molding piece 218 and the second molding piece 220 are pressed together during the formation of the first polymer layer 224, the resulting polymer layer 224 will have a thickness of less than 150 micrometers.

In an example, the thickness of the first polymer layer 224 can be selected based on a particular analyte or analytes an eye-mountable device is configured to detect. For example, an optimal thickness for a first analyte may be 10 micrometers, while an optimal thickness for a second analyte may be 25 micrometers. Other examples are possible as well.

In an example, the polymer material 222 can be any material that can form an eye-compatible polymer layer. For example, the polymer material 222 may be a formulation containing polymerizable monomers, such as hydrogels, silicone hydrogels, silicone elastomers, and rigid gas permeable materials. Further, the polymer material 222 may form a transparent or substantially transparent polymer layer. As such, the use of the polymer material 222 may result in an eye-mountable device through which the wearer can see when mounted on the wearer's eye. In an example, the polymer material 222 can be a hydrogel material, such as silicone hydrogel. As known in the art, hydrogel materials are commonly used in contact-lens technology and are well-suited for eye-mountable devices. Other materials are possible as well. In an example, the structure 202 can be more rigid than the first polymer layer 224.

In an example, the first molding piece 218 and/or the second molding piece 220 can be configured so as to allow sufficient pinch off to provide for suitable edges for an eye-mountable device.

The first polymer layer 224 defines a posterior side 226 of an eye-mountable device. That is, the first polymer layer 224 defines an outer edge of the eye-mountable device. When mounted on an eye of a user, the posterior side 226 of the eye-mountable device defined by the first polymer layer 224 corresponds to a side of the device touching the eye of the user. The first molding piece 218 may be shaped so as to define a shape of the posterior side 226. For example, a curvature of the posterior side 226 may be defined by the first molding piece 218.

The first polymer layer 224 can further comprise an alignment feature 228. In an example, the alignment feature 228 can comprise an asymmetric peg. The asymmetric peg can be a variety of shapes. For instance, the asymmetric peg can have a star-shaped or cross-shaped cross section. Other shapes of the asymmetric peg are possible as well.

As mentioned above, although FIG. 2c illustrates forming the first polymer layer 224 through cast molding, other methods for forming the first polymer layer 224 are possible as well. For example, the first polymer layer 224 may be formed via injection molding. In injection molding, rather than polymer material being compressed between molding pieces, molding material may be heated and injected or otherwise forced into a molding piece or pieces. The injected molding material may then cool and harden to the configuration of the molding piece or pieces.

As another example, the first polymer layer 224 may be formed via spin casting. Through spin-casting techniques, the fabrication device may form a first polymer layer of a precise thickness. In an example, a spin-casting mold may be spun along its central access at a set speed, and the polymer may be introduced to the mold as the mold is spinning in order to form a first polymer layer. The final thickness of the first polymer layer may be influenced by various factors, including but not limited to the spin-casting mold, the amount of polymer introduced to the spin-casting mold, properties of the polymer such as viscosity, and/or the speed at which the spin-casting mold is rotated. These factors may be varied in order to result in a first polymer layer of a well-defined thickness.

C. Positioning the Structure on the First Polymer Layer

Figure 2D:
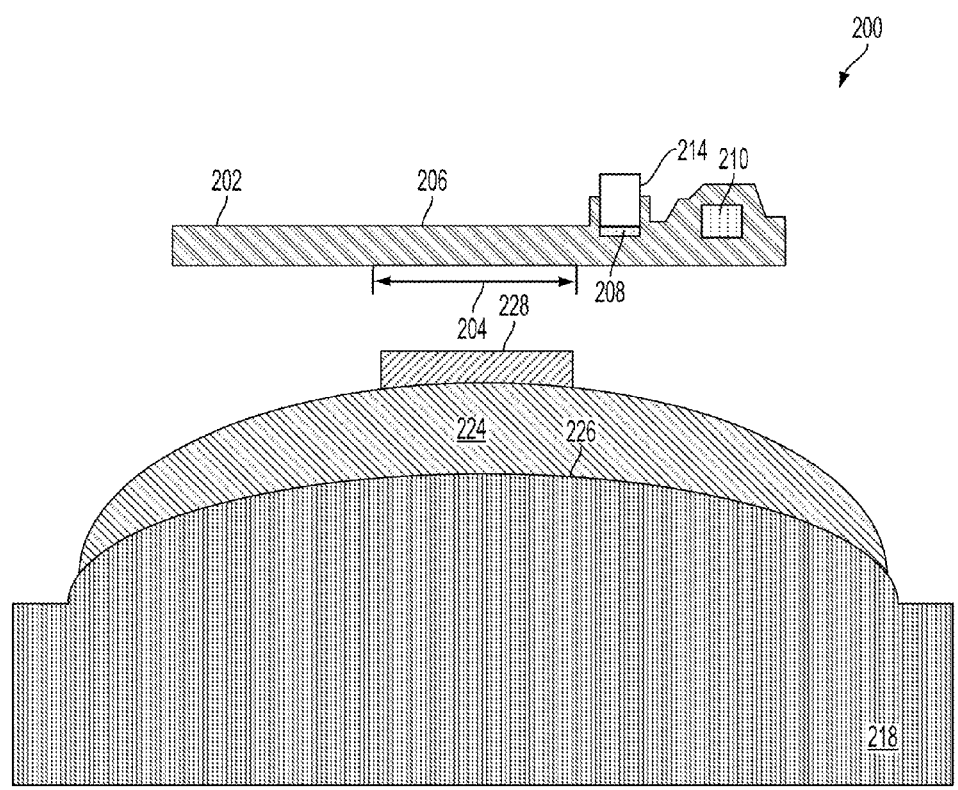
FIG. 2d is an illustration of positioning a structure on a first polymer layer, according to an example embodiment.
Figure 2E:
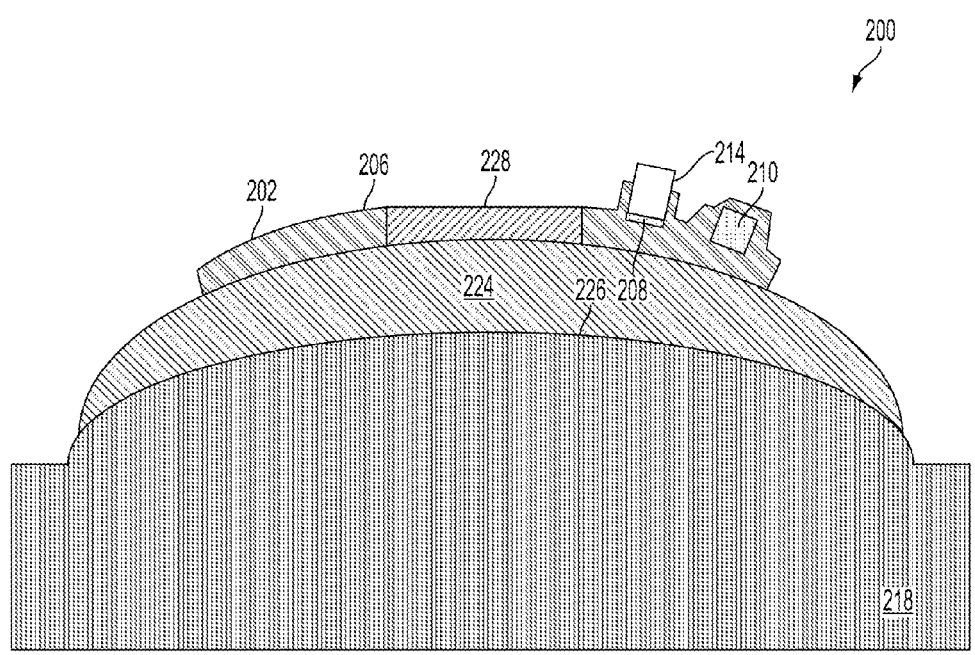
FIG. 2e is an illustration of a structure positioned on a first polymer layer, according to an example embodiment.

As mentioned above, at block 106, a structure may be positioned on the first polymer layer. FIGS. 2d and 2e illustrate an example in which the structure 202 is positioned on the first polymer layer 224.

In order to position the structure 202, the fabrication device 200 may separate the first molding piece 218 from the second molding piece 220. When the fabrication device 200 separates the first molding piece 218 from the second molding piece 220, the first polymer layer 224 may stick to a side of the first molding piece 218. In an example, the first polymer layer 224 and/or the first molding piece 218 can be surface treated, such that the first polymer layer 224 sticks to the side of the first molding piece 218. Additionally or alternatively, the second molding piece 220 can be surface treated, such that the first polymer layer 224 sticks to the side of the first molding piece 218.

In an example, positioning the structure 202 on the first polymer layer 224 can include aligning the structure 202 with the alignment feature 228. In one example, the hole 204 in the structure 202 has an asymmetric inner diameter and the alignment feature 228 includes an asymmetric peg such that the hole 204 receives the alignment feature 228 in only a predetermined rotational orientation. However, other ways of providing a predetermined rotational orientation of the structure 202 by alignment with the alignment feature 228 are also possible.

Alternatively, the fabrication device 200 can include a positioning apparatus (not shown), such as a robotic system, configured to position the structure 202 on the first polymer layer 224 in a predetermined rotational orientation. For instance, the positioning apparatus may (i) pick up the structure 202 (e.g., via suction), (ii) position the structure 202 above the first polymer layer 224, and then (iii) lower the structure 202 toward the first polymer layer 224. When the structure 202 is positioned in a predetermined rotational orientation, the positioning apparatus may then release the structure 202 (e.g., by releasing the suction). With this approach, the first polymer layer 224 might not include the alignment feature 228.

In some embodiments, the positioning apparatus may bend the structure 202. The positioning apparatus may bend the structure 202 by applying a force and/or a torque to one or more portions of the structure 202.

The positioning apparatus may further include a vision system configured to assist with positioning the structure 202 on the first polymer layer 224. Such a vision system may facilitate guiding the structure 202 to a precise location on the first polymer layer 224. In an example, the vision system can be appropriate for situations in which one or more production specifications for an eye-mountable device, such the eye-mountable device 300, have requirements with very low tolerances related to the positioning of a sensor, such as the sensor 208, within the eye-mountable device.

During fabrication of an eye-mountable device, such as the eye-mountable device 300, it may be desirable for the structure 202 to remain in a fixed position during fabrication of the eye-mountable device. For instance, movement of the structure 202 during subsequent formation steps, such as formation of a second polymer layer, may result in improper placement of the structure 202 relative to the surrounding polymer layers. As one example, movement of the structure 202 during filling a mold piece with a polymer material to form the second polymer layer and/or curing the second polymer layer can result in improper placement of the structure 202 relative to the surrounding polymer layers.

Therefore, in an example, an adhesive is applied to the structure 202 and/or the first polymer layer 224 before the structure 202 is placed on the first polymer layer 224. The applied adhesive may facilitate adhesion of the structure 202 to the first polymer layer 224. For instance, a small amount of adhesive may be applied to a cured first polymer layer 224, and the structure 202 may be positioned on the small amount of adhesive such that the structure 202 adheres to the first polymer layer 224. Additionally or alternatively, a small amount of adhesive may be applied to the structure 202, and the structure 202 may then be placed on the first polymer layer 224 (e.g., a cured first polymer layer) such that the structure 202 adheres to the first polymer layer 224. With this arrangement, the structure 202 may remain adhered to the first polymer layer 224 in a secure location during subsequent formation steps.

As noted above, in an example, the first polymer layer 224 in a partially-cured state may have a tackiness that facilitates adhesion thereto. With this arrangement, the structure 202 may remain adhered to the first polymer layer 224 in a secure location during subsequent formation steps.

In some situations, such as for large-scale production purposes, it may be desirable to not only place the structure 202 in a predetermined rotational orientation, but it may also be desirable to repeatedly place and maintain the structure 202 at this precise location for a plurality of eye-mountable devices. Beneficially, fabrication of an eye-mountable device in accordance with an example embodiment allows for such repeatable and precise positioning.

FIG. 2e illustrates the structure 202 positioned on the first polymer layer 224. With this arrangement, the sensor 208 may be mounted at a particular angle along a circumference of the first polymer layer 224. As a result, the sensor 208 may be placed at a precise location in an XYZ plane on the first polymer layer 224. As one example, the sensor 208 may rest at a 6 o'clock position of the first polymer layer 224. As another example, the sensor 208 may rest at a 12 o'clock position of the first polymer layer 224.

Figure 2F:
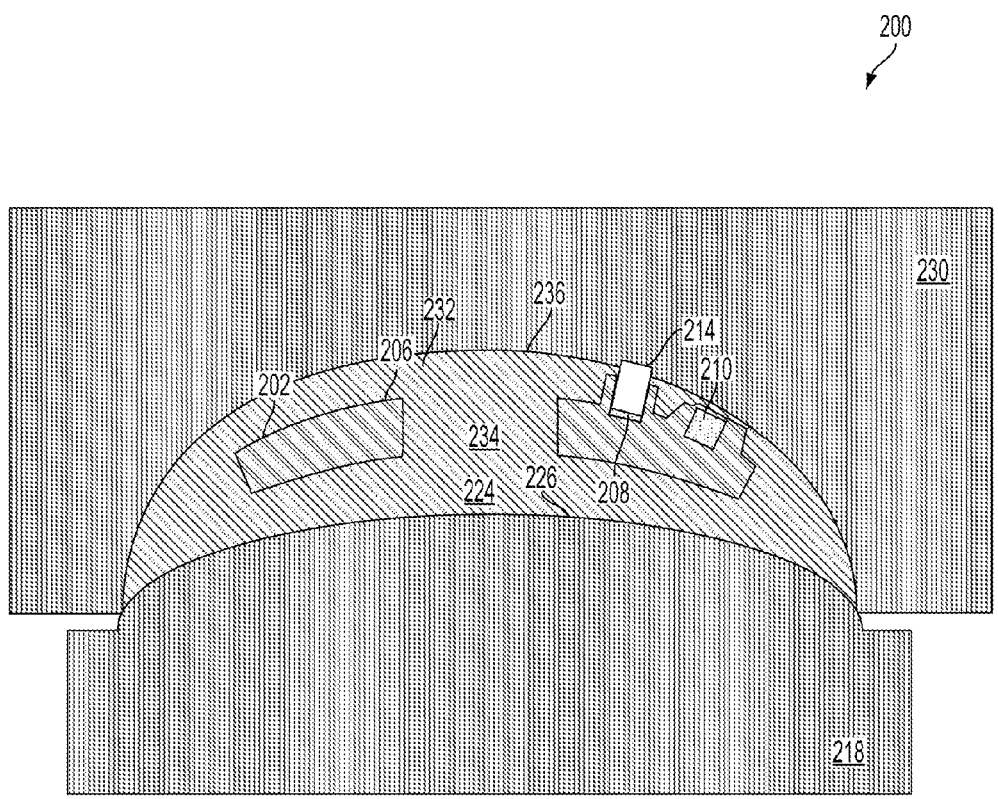
FIG. 2f is an illustration of formation of a second polymer layer, according to an example embodiment.
Figure 2G:
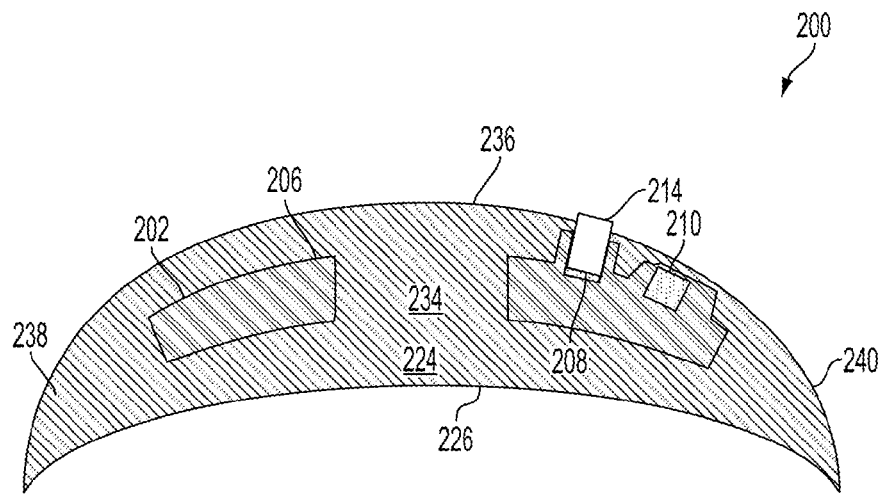
FIG. 2g is an illustration of soaking a partially-fabricated device in a fluid, according to an example embodiment.

D. Forming a Second Polymer Layer Over the First Polymer Layer and the Structure to Provide a Partially-Fabricated Device As mentioned above, at block 108, the fabrication device may form a second polymer layer over the first polymer and the structure to provide a partially-fabricated device. FIG. 2f illustrates the fabrication device 200 including molding pieces that may be used to form the second polymer layer. In particular, FIG. 2f illustrates a third molding piece 230. The first molding piece 218 and the third molding piece 230 may define a second cavity. And FIG. 2g illustrates a partially-fabricated device (or a device) 240.

The first molding piece 218, which already holds the first polymer layer 224 to which the structure 202 is mounted (as illustrated in FIG. 2e), may be filled with a polymer material 232. The polymer material 232 may be formed into a second polymer layer 234 by compression between the first molding piece 218 and the third molding piece 230. However, the cross-linked polymer plug 214 may block the second polymer layer 234 from molding over the sensor 208. As a result, the second polymer layer 234 may mold over the structure 202, such that the structure 202 is fully enclosed by the first polymer layer 224, the second polymer layer 234, and the cross-linked polymer plug 214.

In an example, the third molding piece 230 may contact the cross-linked polymer plug 214 during formation of the second polymer layer 234. With this arrangement, the cross-linked polymer plug 214 can provide a seal during formation of the second polymer layer 234. And as noted above, the cross-linked polymer may be complaint. As a result, when the third molding piece 230 contacts the cross-linked polymer plug 214 during formation of the second polymer layer 234, the cross-linked polymer plug 214 can deform.

After the second polymer layer 234 is formed, the fabrication device 200 may cure the second polymer layer 234. In an example, the second polymer layer 234 can be cured like the first polymer layer 224. However, in other examples, the second polymer layer 234 may be cured by different techniques than the first polymer layer 224. The second polymer layer 234 can be cured by any of the techniques mentioned herein. In an example, the fabrication device 200 may cure the first polymer layer 224 at this stage.

Figure 3:
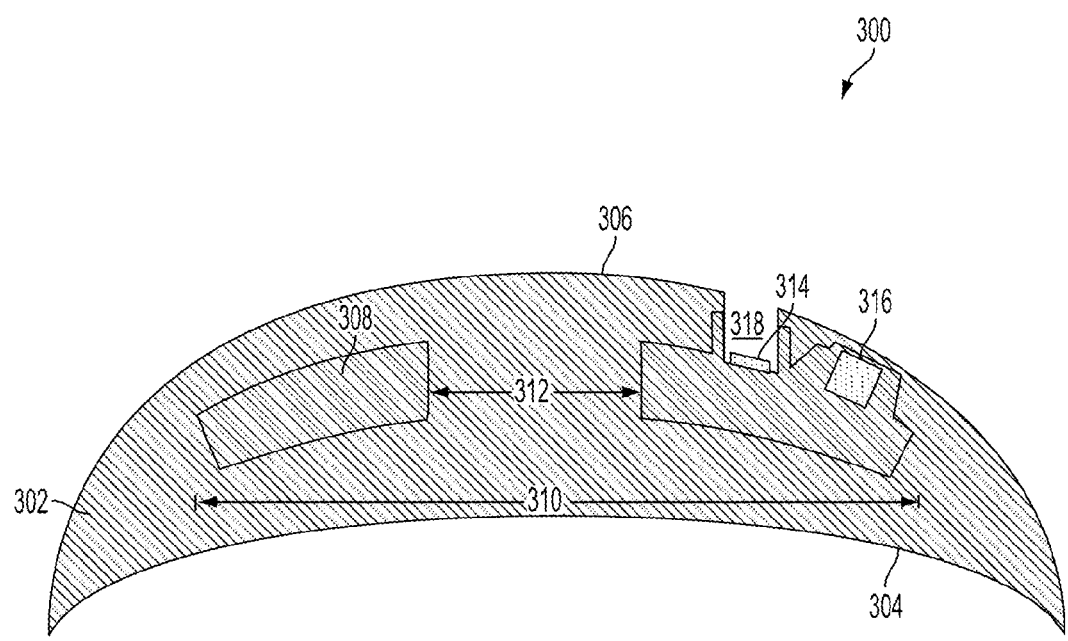
FIG. 3 is an illustration of an eye-mountable device fabricated according to an example embodiment.

After the second polymer layer 234 is cured, there may not be a visible boundary line separating the first polymer layer 224 from the second polymer layer 234. As mentioned above, FIG. 3 illustrates the eye-mountable device 300. In particular, FIG. 3 illustrates the eye-mountable device 300 includes a transparent polymer 302. The transparent polymer 302 can be arranged like the first polymer layer 224 and the second polymer layer 234.

Returning to FIG. 2f, the fabrication device 200 may further comprise one or more alignment pins (not shown), such as a plurality of dowel pins, for aligning the third molding piece 230 and the first molding piece 218. The one or more alignment pins can assist in forming the second polymer layer 234 by aligning the third molding piece 230 with the first molding piece 218.

The first molding piece 218 and the third molding piece 230 may be configured to achieve a given desired thickness of a layer formed between the two cavities. As one example, the first molding piece 218 and the third molding piece 230 may be designed so as to define a thickness of the second polymer layer 234. As another example, the first molding piece 218 and the third molding piece 230 may be designed so as to define a final thickness of an eye-mountable device, such as the eye-mountable device 300. In an example, the first molding piece 218 and the third molding piece 230 can be designed so as to allow for a layer having a given desired thickness between the two pieces (in addition to a thickness of the first polymer 224). As such, when the first molding piece 218 and the third molding piece 230 are pressed together during formation of a layer, the resulting layer will have the given desired thickness.

In an example, the second polymer layer 234 has a thickness of greater than 50 micrometers. However, in other examples, the second polymer layer 234 can have a thickness between 50 and 300 micrometers, such as 130 micrometers. It should be understood that since the second polymer layer 234 molds over the structure 202 except for the cross-linked polymer plug 214, the second polymer layer 234 may not have a uniform thickness. For instance, the thickness of the second polymer layer 234 above the electronics 210 may be less than the thickness of the second polymer layer 234 that is not touching the electronics 210.

In an example, the thickness of the second polymer layer 234 can be selected based on a particular analyte or analytes that the eye-mountable device, such as the eye-mountable device 300, is configured to detect. For example, an optimal thickness for a first analyte may be 10 micrometers, while an optimal thickness for a second analyte may be 25 micrometers. Other examples are possible as well.

In an example, the second polymer layer 234 can be composed of the same polymer material as the first polymer layer 224. However, in other examples, the second polymer layer 234 can be composed of a different polymer material than the first polymer layer 224. The second polymer layer 234 can be any one of the polymer materials mentioned herein. In an example, the structure 202 can be more rigid than the second polymer layer 234.

The second polymer layer 234 defines an anterior side 236 of an eye-mountable device. That is, the second polymer layer 234 defines an outer edge of the eye-mountable device. When mounted on an eye of a user, the anterior side 236 of the eye-mountable device defined by the second polymer layer 234 corresponds to the side of the device that is not touching the eye of the user. The third molding piece 230 may be shaped so as to define a shape of the anterior side 236. For example, a curvature of the anterior side 236 may be defined by the third molding piece 230.

E. Soaking the Partially Fabricated Device in a Fluid

Figure 2H:
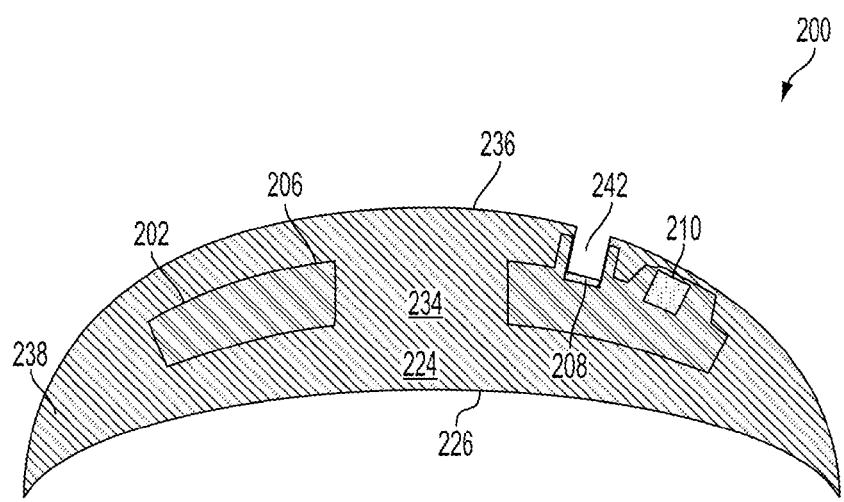
FIG. 2h is an illustration of a partially-fabricated device soaked in a fluid, according to an example embodiment.

As mentioned above, at block 110, the partially-fabricated device is soaked in a fluid, such that the cross-linked polymer plug swells out of the partially-fabricated device to leave a channel in the second polymer layer. FIGS. 2g and 2h illustrate the fabrication device 200 soaking the partially-fabricated device. In particular, FIG. 2g and FIG. 2h illustrate the fabrication device 200 soaking the partially-fabricated device 240, such that the cross-linked polymer plug 214 swells out of the partially-fabricated device 240 to leave a channel 242 in the second polymer layer 234. As shown in FIG. 2g, the partially-fabricated device 240 includes the structure 202, the sensor 208, the electronics 210, the cross-linked polymer plug 214, the posterior side 226, the anterior side 236, and a transparent polymer 238. The transparent polymer 238 includes the first polymer layer 224 and the second polymer layer 234.

In order to soak the partially-fabricated device 240 to leave the channel 242, the fabrication device 200 may separate the first molding piece 218 from the third molding piece 230. When the fabrication device 200 separates the first molding piece 218 from the third molding piece 230, the partially-fabricated device 240 may stick to a side of the first molding piece 218. With this arrangement, the first molding piece 218 can hold the partially-fabricated device 240. In an example, the first polymer layer 224 and/or the first molding piece 218 can be surface treated, such that the partially-fabricated device 240 sticks to the side of the first molding piece 218. Additionally or alternatively, the third molding piece 230 and/or the partially-fabricated device 240 can be surface treated, such that the partially-fabricated device 240 sticks to the side of the first molding piece 218.

After the first molding piece 218 is separated from the third molding piece 230, the partially-fabricated device 240 is removed from the first molding piece 218. In an example, removing the partially-fabricated device 240 from the first mold piece 218 can include the fabrication device 200 removing the surface treatment of the partially-fabricated device 240 and/or the first molding piece 218.

After the partially-fabricated device 240 is removed from the first molding piece 218, the partially-fabricated device 240 is soaked in a fluid, such that the cross-linked polymer plug 214 swells out of the partially-fabricated device 240 to leave the channel 242 in the second polymer layer 234. In an example, the fabrication device 200 can soak the partially-fabricated device 238 in a fluid.

The fluid could take various different forms in various different embodiments. The fluid may selected based on the material of the cross-linked polymer plug 214, the material of the first polymer layer 224, the material of the second polymer layer 234, and/or the material of the polymer 206.

The fluid can include one or more fluids selected from the group consisting of an aqueous solution and an organic solvent. The aqueous solution can be pure water, acidic, basic or buffered, such as phosphate buffered saline. The organic solvent can be a water-miscible solvent, such as tetrahyrofuran (THF), acetone or acetonitrile, a chlorinated sovent, such as dichloromethane or chloroform, or other solvent such as ethyl acetate or hexanes. In some embodiments, the fluid is a homogeneous mixture of an aqueous solution and an organic solvent, such as water/THF or water/acetonitrile.

In another example, the fluid is acidic. In some instances, the fluid includes an organic or inorganic acid in an organic solvent or aqueous solution. In some embodiments, the acidic solution has a pH between 1 and 3. In other instances, the acidic solution has a pH between 3 and 5, while in other instances the acidic solution has a pH between 5 and 7. In some embodiments, the acidic solution has a pH less than 1.

In certain embodiments, the fluid is basic. In some instances, the fluid includes an organic or inorganic base in an organic solvent or aqueous solution. In some embodiments, the basic solution has a pH between 7 and 9. In other instances, the basic solution has a pH between 9 and 11, while in other instances the basic solution has a pH between 11 and 14. In some embodiments, the basic solution has a pH greater than 14.

As mentioned above, FIG. 3 illustrates the eye-mountable device 300 fabricated according to an example embodiment. In particular, FIG. 3 illustrates an anterior side 306 including a channel 318.

In the eye-mountable device 300, a structure 308 is embedded in the transparent polymer 302. The structure 308 has an outer diameter 310 and inner diameter 312 and includes a sensor 314 configured to detect an analyte and electronics 316. The eye-mountable device 300 includes a posterior side 304 and the anterior side 306. The structure 308 may take the form of or be similar in form to the structure 202, the sensor 314 may take the form of or be similar in form to the sensor 208, and the electronics 316 may take the form of or be similar in form to the electronics 210.

In an example, the inner diameter 312 can be asymmetric and define a rotational orientation of the structure 308 relative to the channel 318, such that the sensor 314 is configured to receive the analyte via the channel 318. With this arrangement, the structure 308 is fully enclosed by the transparent polymer 302, except for the sensor 314 being exposed by the channel 318.

In some examples, one or more dimensions of the channel 318 may be based on one or more dimensions of the sensor 314 and/or the electronics 316. As one example, a width of the channel 318 can be based on a width of the sensor 314. As another example, a height of the channel 318 can be based on a height of the electronics 316.

While the body-mountable device has been described as comprising the eye-mountable device 300, the body-mountable device could comprise other mountable devices that are mounted on or in other portions of the human body.

For example, in some embodiments, the body-mountable device may comprise a tooth-mountable device. In some embodiments, the tooth-mountable device may take the form of or be similar in form to the eye-mountable device 300. For instance, the tooth-mountable device may include polymer layers and/or a transparent polymer that are the same or similar to any of the polymer layers and/or the transparent polymers described herein and a structure that is the same or similar to any of the structures described herein. With this arrangement, the tooth-mountable device may be configured to detect at least one analyte in a fluid (e.g., saliva) of a user wearing the tooth-mountable device.

Moreover, in some embodiments, the body-mountable device may comprise a skin-mountable device. In some embodiments, the skin-mountable device may take the form of or be similar in form to the eye-mountable device 300. For instance, the tooth-mountable device may include polymer layers and/or a transparent polymer that are the same or similar to any of the polymer layers and/or the transparent polymers described herein and a structure that is the same or similar to any of the structures described herein. With this arrangement, the skin-mountable device may be configured to detect at least one analyte in a fluid (e.g., perspiration, blood, etc.) of a user wearing the skin-mountable device.

Further, some embodiments may include privacy controls which may be automatically implemented or controlled by the wearer of a body-mountable device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a body-mountable device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

G. Forming the Cross-Linked Polymer Plug when the Structure is Positioned on the First Polymer Layer The example methods described above involve a method of fabricating an eye-mountable device that involves forming a cross-linked polymer plug over a sensor located on a structure, such that the sensor is covered by the cross-linked polymer plug, forming a first polymer layer, and positioning the structure on the first polymer layer. In another example, a cross-linked polymer plug may be formed over a sensor located on a structure when the structure is positioned on a first polymer layer. For instance, in an example where the fabrication device 200 includes an injector as described herein, the injector may inject the polymerizable mixture 216 into the opening 212 when the structure 202 is positioned on the first polymer layer 208.

Figure 4:
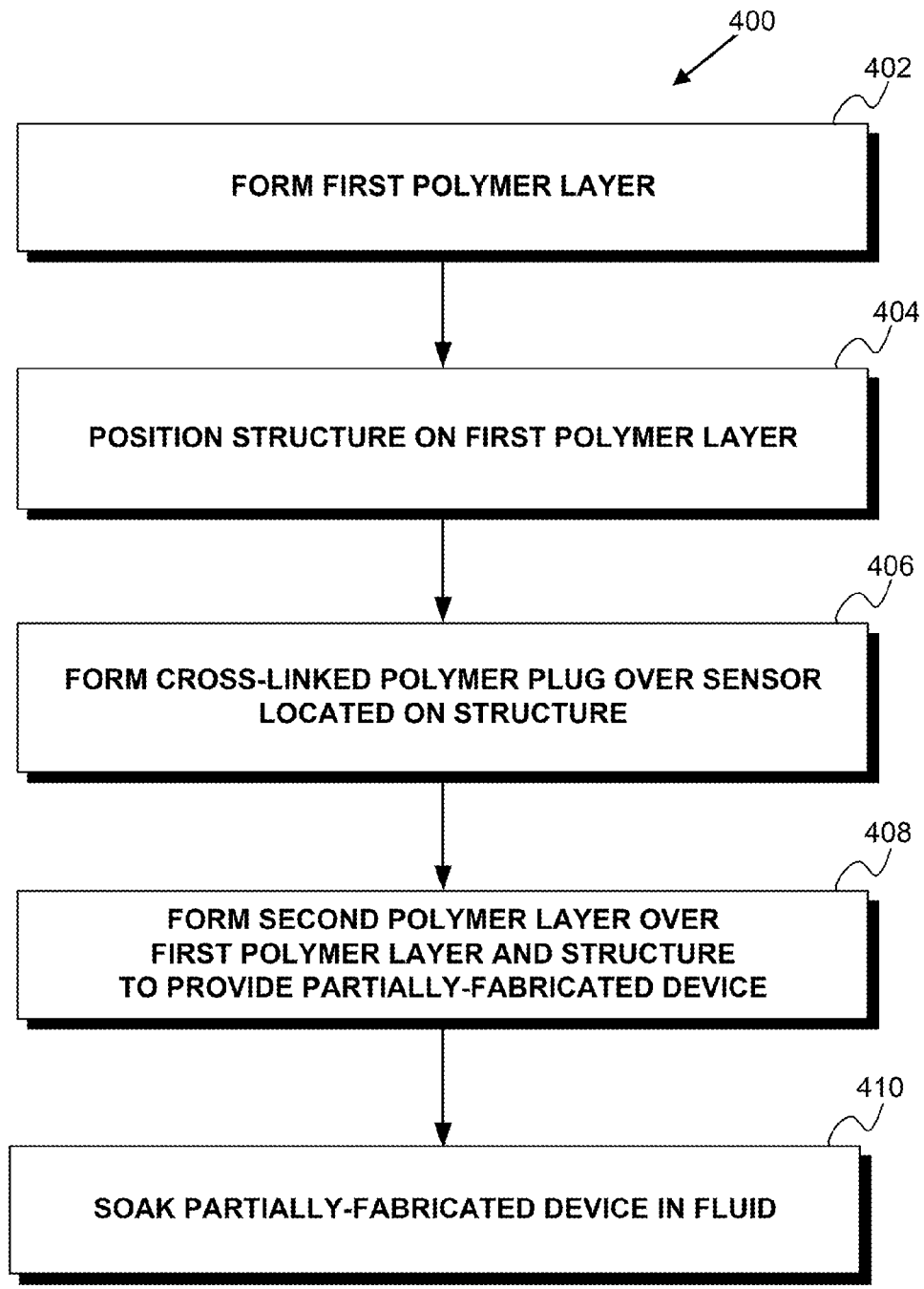
FIG. 4 is a flow chart illustrating another method according to an example embodiment.

FIG. 4 is a flow chart illustrating a method 400 according to an example embodiment. More specifically, the method 400 involves forming a first polymer layer, as shown by block 402. The method 400 may then involve positioning a structure on the first polymer layer, as shown by block 404. The method 400 may then involve forming a cross-linked polymer plug over a sensor located on the structure, such that the sensor is covered by the cross-linked polymer plug, as shown by block 406. The method 400 then may involve forming a second polymer layer over the first polymer layer and the structure to provide a partially-fabricated device in which the structure is fully enclosed by the first polymer layer, the second polymer layer, and the cross-linked polymer plug, as shown by block 408. The method 100 may then involve soaking the partially-fabricated device in a fluid, such that the cross-linked polymer plug swells out of the partially-fabricated device to leave a channel in the second polymer layer, as shown by block 410.

In an example, block 402 may take the form of or be similar in form to block 104, block 404 may take the form of or be similar in form to block 106, block 406 may take the form of or be similar in form to block 102, block 408 may take the form of or be similar in form to block 108, and block 410 may take the form of or be similar in form to block 110.

F. Forming the First Polymer Layer and the Second Polymer Layer at the Same Time The example methods described above involve a method of fabricating an eye-mountable device that involves first forming a first polymer layer and subsequently forming a second polymer layer. In another example, the first polymer layer defining a posterior side of an eye-mountable device and the second polymer layer defining an anterior side of the eye-mountable device may be substantially formed around a structure (e.g., the structure 202) to provide a partially-fabricated device (e.g., the partially-fabricated device 240) at the same time. The term "substantially formed," as used in this disclosure, refers to exactly formed and/or one or more deviations from exactly formed that do not significantly impact leaving a channel in a polymer using a cross-linked polymer plug. Further, in such an example, positioning the structure on the first polymer layer would take place at the same time as the formation of the first polymer layer and the second polymer layer.

Figure 5:
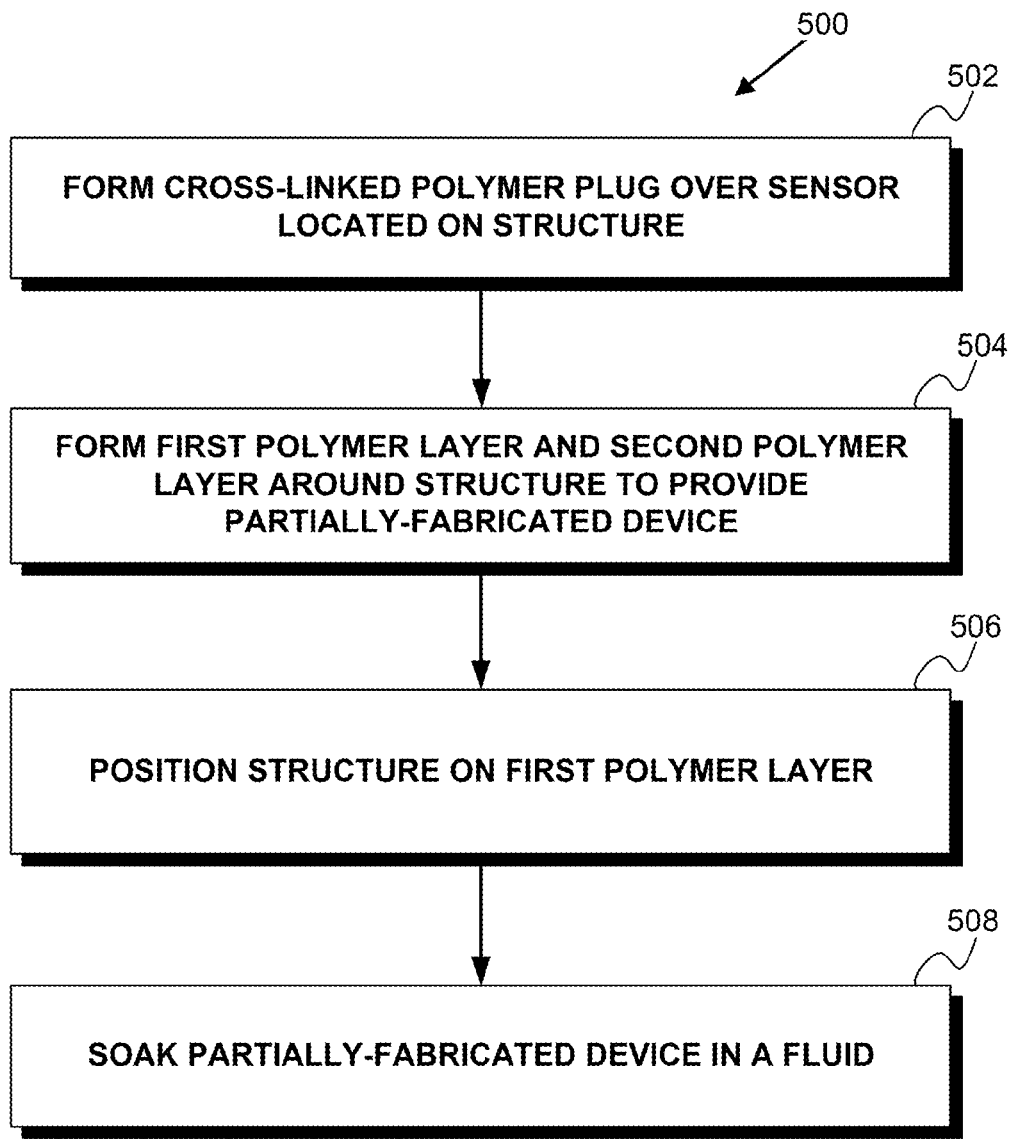
FIG. 5 is a flow chart illustrating yet another method according to an example embodiment.

FIG. 5 is a flow chart illustrating a method 500 according to an example embodiment. More specifically, the method 500 involves forming a cross-linked polymer plug over a sensor located on a structure, such that the sensor is covered by the cross-linked polymer plug, as shown by block 502. The method 500 may then involve forming a first polymer layer and second polymer layer around the structure to provide a partially-fabricated device, as shown by block 504. Further, at the same time as forming a first polymer layer and second polymer around the structure to provide a partially-fabricated device, the method 500 may also involve positioning the structure on the first polymer layer, as shown by block 506. The method 500 may then involve soaking the partially-fabricated device in a fluid, such that the cross-linked polymer plug swells out of the partially-fabricated device to leave a channel in the second polymer layer, as shown in block 508. In an example, block 502 may take the form of or be similar in form to block 102, and block 508 may take the form of or be similar in form to block 110.

For instance, in accordance with an example embodiment, at blocks 504 and 506, the fabrication device may be configured to position a structure within a mold cavity or cavities, and the fabrication device may then form the first polymer layer and the second polymer layer around the structure. In such an example, the fabrication device may be configured to inject mold into the molding cavity, and the injective mold may encapsulate the structure. In this example, the fabrication device may include a molding cavity or cavities that have at least one opening configured to allow the fabrication device to hold the structure in place as the first and second polymer layers are formed around the structure. The molding cavity or cavities may be filled with the polymer material, and this introduction of the polymer material may form the polymer layers around the structure.

III. Example Systems and Eye-Mountable Devices

As mentioned above, a body-mountable device may be fabricated using the example methods described above. Further, the body-mountable device may be configured to monitor health-related information based on at least one analyte detected in a fluid of a user wearing the body-mountable device. An eye-mountable device configured to monitor health-related information based on at least one analyte detected from an eye of a user is described in greater detail below with reference to FIGS. 6 and 7a-d.

A structure in accordance with an exemplary embodiment may include a sensor, electronics, and an antenna all situated on a substrate. The electronics may operate the sensor to perform readings and operate the antenna to wirelessly communicate the readings from the sensor to an external reader via the antenna. The sensor can be arranged on the substrate to face outward, away from the corneal surface of the user, so as to generate clinically relevant readings from tear fluid of the user that the sensor receives via a channel in the anterior side of the eye-mountable device. For example, the sensor can be suspended in the lens material and situated such that the sensor is less than 10 micrometers from the anterior edge of the eye-mountable device. The sensor can generate an output signal indicative of a concentration of an analyte that the sensor receives via the channel.

Figure 6:
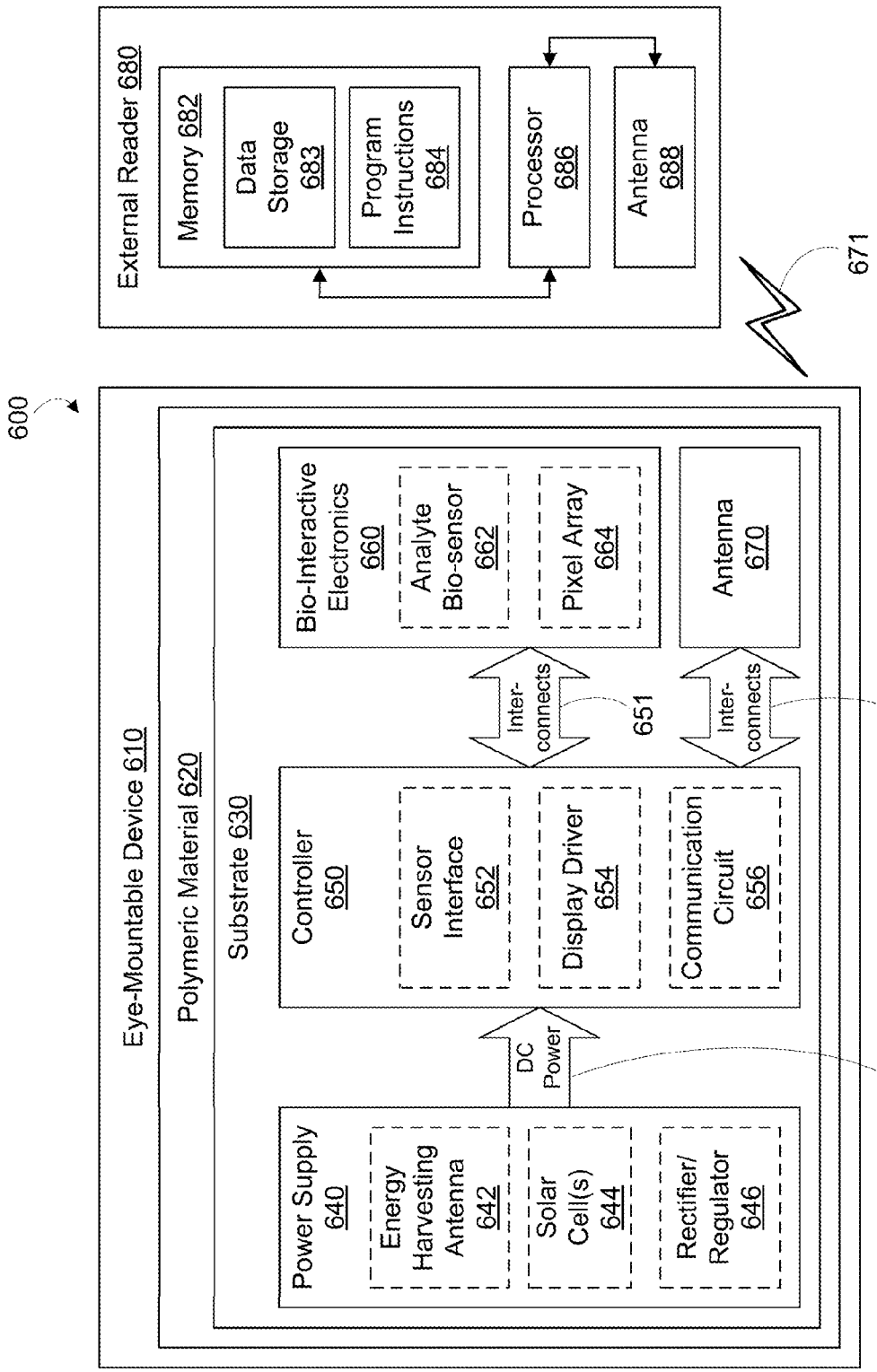
FIG. 6 is a block diagram of a system with an eye-mountable device in wireless communication with an external reader, according to an example embodiment.

FIG. 6 is a block diagram of a system 600 with an eye-mountable device 610 in wireless communication with an external reader 680. The exposed regions of the eye-mountable device 610 are made of a polymeric material 620 formed to be contact-mounted to a corneal surface of an eye. In accordance with the exemplary methods, polymeric material 620 may comprise a first polymer layer and a second polymer layer.

Substrate 630 is embedded in the polymeric material 620 to provide a mounting surface for a power supply 640, a controller 650, bio-interactive electronics 660, and an antenna 670. The bio-interactive electronics 660 are operated by the controller 650. The power supply 640 supplies operating voltages to the controller 650 and/or the bio-interactive electronics 660. The antenna 670 is operated by the controller 650 to communicate information to and/or from the eye-mountable device 610. The antenna 670, the controller 650, the power supply 640, and the bio-interactive electronics 660 can all be situated on the embedded substrate 630. Because the eye-mountable device 610 includes electronics and is configured to be contact-mounted to an eye, it may also be referred to as an ophthalmic electronics platform.

To facilitate contact-mounting, the polymeric material 620 can have a concave surface configured to adhere ("mount") to a moistened corneal surface (e.g., by capillary forces with a tear film coating the corneal surface). Additionally or alternatively, the eye-mountable device 610 can be adhered by a vacuum force between the corneal surface and the polymeric material due to the concave curvature. While mounted with the concave surface against the eye, the anterior or outward-facing surface of the polymeric material 620 can have a convex curvature that is formed to not interfere with eye-lid motion while the eye-mountable device 610 is mounted to the eye. For example, the polymeric material 620 can be a substantially transparent curved polymeric disk shaped similarly to a contact lens.

The polymeric material 620 can include one or more biocompatible materials, such as those employed for use in contact lenses or other ophthalmic applications involving direct contact with the corneal surface. The polymeric material 620 can optionally be formed in part from such biocompatible materials or can include an outer coating with such biocompatible materials. The polymeric material 620 can include materials configured to moisturize the corneal surface, such as hydrogels and the like. In some instances, the polymeric material 620 can be a deformable ("non-rigid") material to enhance wearer comfort. In some instances, the polymeric material 620 can be shaped to provide a predetermined, vision-correcting optical power, such as can be provided by a contact lens.

The substrate 630 includes one or more surfaces suitable for mounting the bio-interactive electronics 660, the controller 650, the power supply 640, and the antenna 670. The substrate 630 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) can be patterned on the substrate 630 to form circuitry, electrodes, etc. For example, the antenna 670 can be formed by depositing a pattern of gold or another conductive material on the substrate 630. Similarly, interconnects 651, 657 between the controller 650 and the bio-interactive electronics 660, and between the controller 650 and the antenna 670, respectively, can be formed by depositing suitable patterns of conductive materials on the substrate 630. A combination of resists, masks, and deposition techniques can be employed to pattern materials on the substrate 630.

The substrate 630 can be a relatively rigid polymeric material, such as polyethylene terephthalate ("PET"), paralyene or another material sufficient to structurally support the circuitry and/or electronics within the polymeric material 620. The eye-mountable device 610 can alternatively be arranged with a group of unconnected substrates rather than a single substrate. For example, the controller 650 and a bio-sensor or other bio-interactive electronic component can be mounted to one substrate, while the antenna 670 is mounted to another substrate and the two can be electrically connected via the interconnects 657.

In some embodiments, the bio-interactive electronics 660 (and the substrate 630) can be positioned away from the center of the eye-mountable device 610 and thereby avoid interference with light transmission to the eye through the center of the eye-mountable device 610. For example, where the eye-mountable device 610 is shaped as a concave-curved disk, the substrate 630 can be embedded around the periphery (e.g., near the outer circumference) of the disk. In some embodiments, the bio-interactive electronics 660 (and the substrate 630) can be positioned in the center region of the eye-mountable device 610. The bio-interactive electronics 660 and/or the substrate 630 can be substantially transparent to incoming visible light to mitigate interference with light transmission to the eye. Moreover, in some embodiments, the bio-interactive electronics 660 can include a pixel array 664 that emits and/or transmits light to be perceived by the eye according to display driver instructions. Thus, the bio-interactive electronics 660 can optionally be positioned in the center of the eye-mountable device so as to generate perceivable visual cues to a wearer of the eye-mountable device 610, such as by displaying information via the pixel array 664.

The substrate 630 can be shaped as a flattened ring with a radial width dimension sufficient to provide a mounting platform for the embedded electronics components. The substrate 630 can have a thickness sufficiently small to allow the substrate 630 to be embedded in the polymeric material 620 without influencing the profile of the eye-mountable device 610. The substrate 630 can have a thickness sufficiently large to provide structural stability suitable for supporting the electronics mounted thereon. For example, the substrate 630 can be shaped as a ring with a diameter of about 10 millimeters, a radial width of about 1 millimeter (e.g., an outer radius 1 millimeter larger than an inner radius), and a thickness of about 50 micrometers. The substrate 630 can optionally be aligned with the curvature of the anterior side of the eye-mountable device 610.

The power supply 640 is configured to harvest ambient energy to power the controller 650 and bio-interactive electronics 660. For example, a radio-frequency energy harvesting antenna 642 can capture energy from incident radio radiation. Additionally or alternatively, solar cell(s) 644 ("photovoltaic cells") can capture energy from incoming ultraviolet, visible, and/or infrared radiation. Furthermore, an inertial power scavenging system can be included to capture energy from ambient vibrations. The energy harvesting antenna 642 can optionally be a dual-purpose antenna that is also used to communicate information to the external reader 680. That is, the functions of the antenna 670 and the energy harvesting antenna 642 can be accomplished with the same physical antenna.

A rectifier/regulator 646 can be used to condition the captured energy to a stable DC supply voltage 641 that is supplied to the controller 650. For example, the energy harvesting antenna 642 can receive incident radio frequency radiation. Varying electrical signals on the leads of the antenna 642 are output to the rectifier/regulator 646. The rectifier/regulator 646 rectifies the varying electrical signals to a DC voltage and regulates the rectified DC voltage to a level suitable for operating the controller 650. Additionally or alternatively, output voltage from the solar cell(s) 644 can be regulated to a level suitable for operating the controller 650. The rectifier/regulator 646 can include one or more energy storage devices arranged to mitigate high frequency variations in the ambient energy harvesting antenna 642 and/or solar cell(s) 644. For example, an energy storage device (e.g., capacitor, inductor, etc.) can be connected to the output of the rectifier/regulator 646 so as to function as a low-pass filter.

The controller 650 is turned on when the DC supply voltage 641 is provided to the controller 650, and the logic in the controller 650 operates the bio-interactive electronics 660 and the antenna 670. The controller 650 can include logic circuitry configured to operate the bio-interactive electronics 660 so as to interact with a biological environment of the eye-mountable device 610. The interaction could involve the use of one or more components, such as an analyte bio-sensor 662, in bio-interactive electronics 660 to obtain input from the biological environment. Alternatively or additionally, the interaction could involve the use of one or more components, such as the pixel array 664, to provide an output to the biological environment.

In one example, a sensor interface module 652 can be included for operating the analyte bio-sensor 662. The analyte bio-sensor 662 can be, for example, an amperometric electrochemical sensor that includes a working electrode and a reference electrode. Application of an appropriate voltage between the working and reference electrodes can cause an analyte to undergo electrochemical reactions (e.g., reduction and/or oxidation reactions) at the working electrode to generate an amperometric current. The amperometric current can be dependent on the analyte concentration, and thus the amount of amperometric current can provide an indication of analyte concentration. In some embodiments, the sensor interface module 652 can be a potentiostat configured to apply a voltage difference between the working and reference electrodes while measuring a current through the working electrode.

In some instances, a reagent can also be included to sensitize the electrochemical sensor to desired analytes. For example, a layer of glucose oxidase ("GOD") can be situated around the working electrode to catalyze glucose into hydrogen peroxide ($H_2O_2$). The hydrogen peroxide can then be oxidized at the working electrode, which releases electrons to the working electrode, which generates a current.

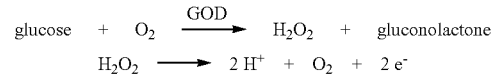

The current generated by either reduction or oxidation reactions can be approximately proportionate to the reaction rate. Further, the reaction rate can be dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate can be approximately proportionate to the concentration of the analyte molecules. The current can thus provide an indication of the analyte concentration.

The controller 650 can optionally include a display driver module 654 for operating the pixel array 664. The pixel array 664 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 654. Such a pixel array 664 can also optionally include more than one color of pixels (e.g., red, green, and blue pixels) to render visual content in color. The display driver module 654 can include, for example, one or more data lines providing programming information to the separately programmed pixels in the pixel array 664 and one or more addressing lines for setting groups of pixels to receive such programming information. Such a pixel array 664 situated on the eye can also include one or more lenses to direct light from the pixel array to a focal plane perceivable by the eye.

The controller 650 can also include a communication circuit 656 for sending and/or receiving information via the antenna 670. The communication circuit 656 can optionally include one or more oscillators, mixers, frequency injectors, etc. to modulate and/or demodulate information on a carrier frequency to be transmitted and/or received by the antenna 670. In some examples, the eye-mountable device 610 is configured to indicate an output from a bio-sensor by modulating an impedance of the antenna 670 in a manner that is perceivable by the external reader 680. For example, the communication circuit 656 can cause variations in the amplitude, phase, and/or frequency of backscatter radiation from the antenna 670, and such variations can be detected by the external reader 680.

The controller 650 is connected to the bio-interactive electronics 660 via interconnects 651. For example, where the controller 650 includes logic elements implemented in an integrated circuit to form the sensor interface module 652 and/or display driver module 654, a patterned conductive material (e.g., gold, platinum, palladium, titanium, copper, aluminum, silver, metals, combinations of these, etc.) can connect a terminal on the chip to the bio-interactive electronics 660. Similarly, the controller 650 is connected to the antenna 670 via interconnects 657.

It is noted that the block diagram shown in FIG. 6 is described in connection with functional modules for convenience in description. However, embodiments of the eye-mountable device 610 can be arranged with one or more of the functional modules ("sub-systems") implemented in a single chip, integrated circuit, and/or physical feature. For example, while the rectifier/regulator 646 is illustrated in the power supply block 640, the rectifier/regulator 646 can be implemented in a chip that also includes the logic elements of the controller 650 and/or other features of the embedded electronics in the eye-mountable device 610. Thus, the DC supply voltage 641 that is provided to the controller 650 from the power supply 640 can be a supply voltage that is provided on a chip by rectifier and/or regulator components of the same chip. That is, the functional blocks in FIG. 6 shown as the power supply block 640 and controller block 650 need not be implemented as separated modules. Moreover, one or more of the functional modules described in FIG. 6 can be implemented by separately packaged chips electrically connected to one another.

Additionally or alternatively, the energy harvesting antenna 642 and the antenna 670 can be implemented with the same physical antenna. For example, a loop antenna can both harvest incident radiation for power generation and communicate information via backscatter radiation.

The external reader 680 includes an antenna 688 (or group of more than one antennae) to send and receive wireless signals 671 to and from the eye-mountable device 610. The external reader 680 also includes a computing system with a processor 686 in communication with a memory 682. The memory 682 is a non-transitory computer-readable medium that can include, without limitation, magnetic disks, optical disks, organic memory, and/or any other volatile (e.g., RAM) or non-volatile (e.g., ROM) storage system readable by the processor 686. The memory 682 can include a data storage 683 to store indications of data structures, such as sensor readings (e.g., from the analyte bio-sensor 662), program settings (e.g., to adjust behavior of the eye-mountable device 610 and/or external reader 680), etc. The memory can also include program instructions 684 for execution by the processor 686 to cause the external reader to perform processes specified by the program instructions 684. For example, the program instructions 684 can cause external reader 680 to provide a user interface that allows for retrieving information communicated from the eye-mountable device 610 (e.g., sensor outputs from the analyte bio-sensor 662). The external reader 680 can also include one or more hardware components for operating the antenna 688 to send and receive the wireless signals 671 to and from the eye-mountable device 610. For example, oscillators, frequency injectors, encoders, decoders, amplifiers, filters, etc. can drive the antenna 688 according to instructions from the processor 686.

The external reader 680 can be a smart phone, digital assistant, or other portable computing device with wireless connectivity sufficient to provide the wireless communication link 671. The external reader 680 can also be implemented as an antenna module that can be plugged in to a portable computing device, such as in an example where the communication link 671 operates at carrier frequencies not commonly employed in portable computing devices. In some instances, the external reader 680 is a special-purpose device configured to be worn relatively near a wearer's eye to allow the wireless communication link 671 to operate with a low power budget. For example, the external reader 680 can be integrated in a piece of jewelry such as a necklace, earing, etc. or integrated in an article of clothing worn near the head, such as a hat, headband, etc.

In an example where the eye-mountable device 610 includes an analyte bio-sensor 662, the system 600 can be operated to monitor the analyte concentration in tear film on the surface of the eye. Thus, the eye-mountable device 610 can be configured as a platform for an ophthalmic analyte bio-sensor. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 600 configured as a tear film analyte monitor, the external reader 680 can emit radio frequency radiation 671 that is harvested to power the eye-mountable device 610 via the power supply 640. Radio frequency electrical signals captured by the energy harvesting antenna 642 (and/or the antenna 670) are rectified and/or regulated in the rectifier/regulator 646 and a regulated DC supply voltage 647 is provided to the controller 650. The radio frequency radiation 671 thus turns on the electronic components within the eye-mountable device 610. Once turned on, the controller 650 operates the analyte bio-sensor 662 to measure an analyte concentration level. For example, the sensor interface module 652 can apply a voltage between a working electrode and a reference electrode in the analyte bio-sensor 662 sufficient to cause the analyte to undergo an electrochemical reaction at the working electrode. The current through the working electrode can be measured to provide the sensor output indicative of the analyte concentration. The controller 650 can operate the antenna 670 to communicate the sensor results back to the external reader 680 (e.g., via the communication circuit 656). The sensor result can be communicated by, for example, modulating an impedance of the antenna 670 such that the modulation in impedance is detected by the external reader 680. The modulation in antenna impedance can be detected by, for example, backscatter radiation from the antenna 670.

In some embodiments, the system 600 can operate to non-continuously ("intermittently") supply energy to the eye-mountable device 610 to power the on-board controller 650 and electronics 660. For example, radio frequency radiation 671 can be supplied to power the eye-mountable device 610 long enough to carry out a tear film analyte concentration measurement and communicate the results. For example, the supplied radio frequency radiation can provide sufficient power to charge two electrodes to a potential sufficient to induce electrochemical reactions, measure the resulting amperometric current, and modulate the antenna impedance to adjust the backscatter radiation in a manner indicative of the measured current. In such an example, the supplied radio frequency radiation 671 can be considered an interrogation signal from the external reader 680 to the eye-mountable device 610 to request a measurement. By periodically interrogating the eye-mountable device 610 (e.g., by supplying radio frequency radiation 671 to temporarily turn the device on) and storing the sensor results (e.g., via the data storage 683), the external reader 680 can accumulate a set of analyte concentration measurements over time without continuously powering the eye-mountable device 610.

Figure 7A:
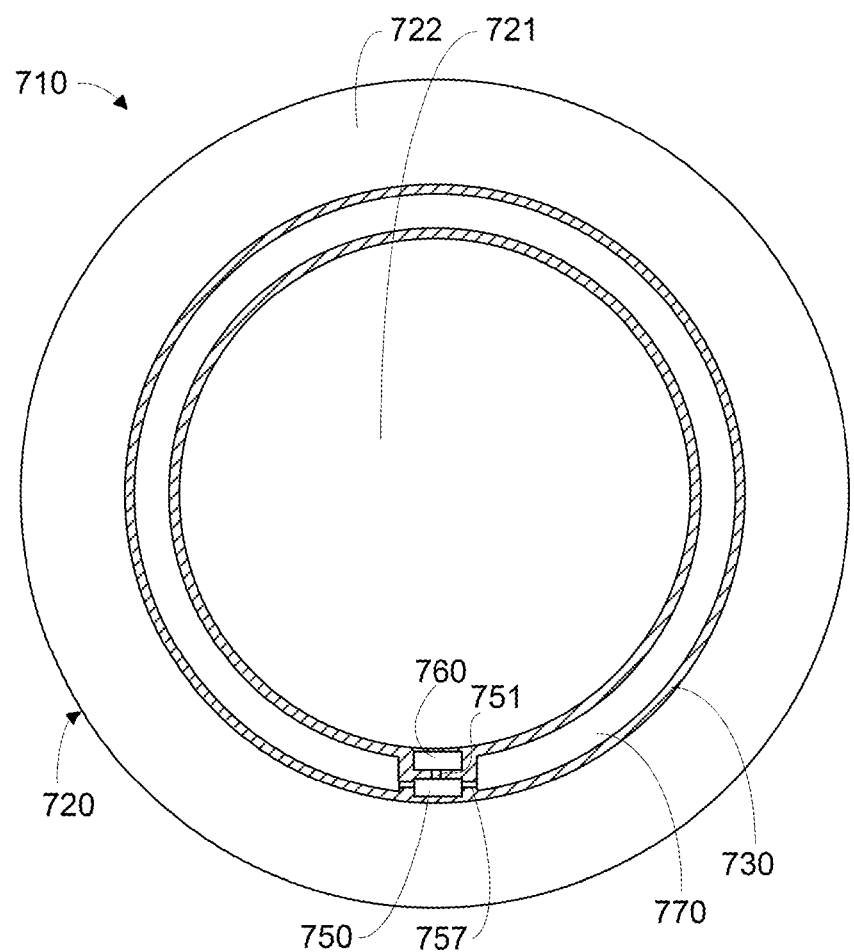
FIG. 7a is a top view of an eye-mountable device, according to an example embodiment.
Figure 7B:
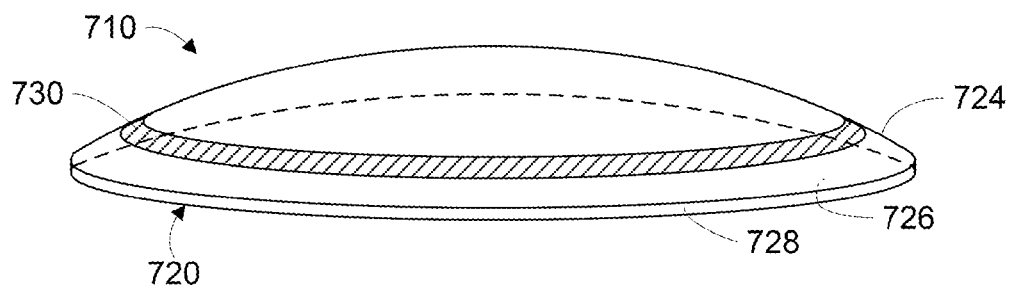
FIG. 7b is a side view of an eye-mountable device, according to an example embodiment.

FIG. 7a is a top view of an eye-mountable electronic device 710. FIG. 7b is a side view of the eye-mountable electronic device shown in FIG. 7a. It is noted that relative dimensions in FIGS. 7a and 7b are not necessarily to scale, but have been rendered for purposes of explanation only in describing the arrangement of the eye-mountable electronic device 710. The eye-mountable device 710 is formed of a polymeric material 720 shaped as a curved disk. The polymeric material 720 can be a substantially transparent material to allow incident light to be transmitted to the eye while the eye-mountable device 710 is mounted to the eye. The polymeric material 720 can be a biocompatible material similar to those employed to form vision correction and/or cosmetic contact lenses in optometry, such as polyethylene terephthalate ("PET"), polymethyl methacrylate ("PMMA"), silicone hydrogels, combinations of these, etc. The polymeric material 720 can be formed with one side having a concave surface 726 suitable to fit over a corneal surface of an eye. The opposing side of the disk can have a convex surface 724 that does not interfere with eyelid motion while the eye-mountable device 710 is mounted to the eye. A circular outer side edge 728 connects the concave surface 724 and convex surface 726.

The eye-mountable device 710 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 710 can be selected according to the size and/or shape of the corneal surface and/or the scleral surface of the wearer's eye.

While the eye-mountable device 710 is mounted in an eye, the convex surface 724 (i.e., the anterior surface) faces outward to the ambient environment while the concave surface 726 (i.e., the posterior surface) faces inward, toward the corneal surface. The convex surface 724 can therefore be considered an outer, top surface of the eye-mountable device 710 whereas the concave surface 726 can be considered an inner, bottom surface. The "top" view shown in FIG. 7a is facing the convex surface 724.

A substrate 730 is embedded in the polymeric material 720. The substrate 730 can be embedded to be situated along the outer periphery 722 of the polymeric material 720, away from the center region 721. The substrate 730 does not interfere with vision because it is too close to the eye to be in focus and is positioned away from the center region 721 where incident light is transmitted to the eye-sensing portions of the eye. Moreover, the substrate 730 can be formed of a transparent material to further mitigate any effects on visual perception.

The substrate 730 can be shaped as a flat, circular ring (e.g., a disk with a central hole). The flat surface of the substrate 730 (e.g., along the radial width) is a platform for mounting electronics such as chips (e.g., via flip-chip mounting) and for patterning conductive materials (e.g., via deposition techniques) to form electrodes, antenna(e), and/or connections. The substrate 730 and the polymeric material 720 can be approximately cylindrically symmetric about a common central axis. The substrate 730 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only. The substrate 730 can be implemented in a variety of different form factors.

A loop antenna 770, a controller 750, and bio-interactive electronics 760 are disposed on the embedded substrate 730. The controller 750 can be a chip including logic elements configured to operate the bio-interactive electronics 760 and the loop antenna 770. The controller 750 is electrically connected to the loop antenna 770 by interconnects 757 also situated on the substrate 730. Similarly, the controller 750 is electrically connected to the bio-interactive electronics 760 by interconnects 751. The interconnects 751, 757, the loop antenna 770, and any conductive electrodes (e.g., for an electrochemical analyte bio-sensor, etc.) can be formed from conductive materials patterned on the substrate 730 by a process for precisely patterning such materials, such as deposition or lithography. The conductive materials patterned on the substrate 730 can be, for example, gold, platinum, palladium, titanium, carbon, aluminum, copper, silver, silver-chloride, and/or other materials.

With reference to FIG. 7a, which is a view facing the convex surface 724 of the eye-mountable device 710, the bio-interactive electronics 760 is mounted to a side of the substrate 730 facing the convex surface 724. Where the bio-interactive electronics 760 includes an analyte bio-sensor, for example, mounting such a bio-sensor on the substrate 730 facing the convex surface 724 allows the bio-sensor to receive analyte concentrations in tear film through a channel 772 in the polymeric material 720 to the convex surface 724 (as shown in FIGS. 7c and 7d). In some embodiments, some electronic components can be mounted on one side of the substrate 730, while other electronic components are mounted to the opposing side, and connections between the two can be made through conductive materials passing through the substrate 730.

The loop antenna 770 is a layer of conductive material patterned along the flat surface of the substrate to form a flat conductive ring. In some instances, the loop antenna 770 can be formed without making a complete loop. For instance, the loop antenna 770 can have a cutout to allow room for the controller 750 and the bio-interactive electronics 760, as illustrated in FIG. 7a. However, the loop antenna 770 can also be arranged as a continuous strip of conductive material that wraps entirely around the flat surface of the substrate 730 one or more times. For example, a strip of conductive material with multiple windings can be patterned on the side of the substrate 730 opposite the controller 750 and bio-interactive electronics 760. Interconnects between the ends of such a wound antenna (e.g., the antenna leads) can be passed through the substrate 730 to the controller 750. In some embodiments, the loop antenna can include a plurality of conductive loops spaced apart from each other, such as three conductive loops, five conductive loops, nine conductive loops, etc. With such an arrangement, the polymeric material 720 may extend between adjacent conductive loops in the plurality of conductive loops.

FIG. 7c is a side cross-section view of the eye-mountable electronic device 710 while mounted to a corneal surface 784 of an eye 780. FIG. 7d is a close-in side cross-section view enhanced to show tear film layers 790, 792 surrounding the exposed surfaces 724, 726 of the eye-mountable device 710. It is noted that relative dimensions in FIGS. 7c and 7d are not necessarily to scale, but have been rendered for purposes of explanation only in describing the arrangement of the eye-mountable electronic device 710. For example, the total thickness of the eye-mountable device 710 can be about 200 micrometers, while the thickness of the tear film layers 790, 792 can each be about 10 micrometers, although this ratio is may not be reflected in the drawings. Some aspects are exaggerated to allow for illustration and facilitate explanation.

The eye 780 includes a cornea 782 that is covered by bringing the upper eyelid 786 and lower eyelid 788 together over the top of the eye 780. Incident light is received by the eye 780 through the cornea 782, where light is optically directed to light sensing elements of the eye 780 (e.g., rods and cones, etc.) to stimulate visual perception. The motion of the eyelids 786, 788 distributes a tear film across the exposed corneal surface 784 of the eye 780. The tear film is an aqueous solution secreted by the lacrimal gland to protect and lubricate the eye 780. When the eye-mountable device 710 is mounted in the eye 780, the tear film coats both the convex and concave surfaces 724, 726 with an inner layer 790 (along the concave surface 726) and an outer layer 792 (along the convex layer 724). The tear film layers 790, 792 can be about 10 micrometers in thickness and together account for about 10 microliters.

The tear film layers 790, 792 are distributed across the corneal surface 784 and/or the convex surface 724 by motion of the eyelids 786, 788. For example, the eyelids 786, 788 raise and lower, respectively, to spread a small volume of tear film across the corneal surface 784 and/or the convex surface 724 of the eye-mountable device 710. The tear film layer 790 on the corneal surface 784 also facilitates mounting the eye-mountable device 710 by capillary forces between the concave surface 726 and the corneal surface 784. In some embodiments, the eye-mountable device 710 can also be held over the eye in part by vacuum forces against the corneal surface 784 due to the concave curvature of the eye-facing concave surface 726.

As shown in the cross-sectional views in FIGS. 7c and 7d, the substrate 730 can be inclined such that the flat mounting surfaces of the substrate 730 are approximately parallel to the adjacent portion of the convex surface 724. As described above, the substrate 730 is a flattened ring with an inward-facing surface 732 (facing the concave surface 726 of the polymeric material 720) and an outward-facing surface 734 (facing the convex surface 724). The substrate 730 can have electronic components and/or patterned conductive materials mounted to either or both mounting surfaces 732, 734.

As shown in FIG. 7d, the bio-interactive electronics 760, the controller 750, and the conductive interconnect 751 are located between the outward-facing surface 734 and the inward-facing surface 732 such that the bio-interactive electronics 760 are facing the convex surface 724. As described above, the polymer layer defining the anterior side may be greater than 50 micrometers thick, whereas the polymer layer defining the posterior side may be less than 150 micrometers. Thus, the bio-interactive electronics 760 may be at least 50 micrometers away from the convex surface 724 and may be a greater distance away from the concave surface 726. However, in other examples, the bio-interactive electronics 760 may be mounted on the inward-facing surface 732 of the substrate 730 such that the bio-interactive electronics 760 are facing the concave surface 726. The bio-interactive electronics 760 could also be positioned closer to the concave surface 726 than the convex surface 724. With this arrangement, the bio-interactive electronics 760 can receive analyte concentrations in the tear film 792 through the channel 772.

While the body-mountable device has been described as comprising the eye-mountable device 610 and/or the eye-mountable device 710, the body-mountable device could comprise other mountable devices that are mounted on or in other portions of the body.

As noted, in some embodiments, the body-mountable device may comprise a tooth-mountable device. In some embodiments, the tooth-mountable device may take the form of or be similar in form to the eye-mountable device 610 and/or the eye-mountable device 710. For instance, the tooth-mountable device may include a polymeric material that is the same or similar to any of the polymeric materials described herein and a substrate that is the same or similar to any of the substrates described herein.

As noted, in some embodiments, the body-mountable device may comprise a skin-mountable device. In some embodiments, the skin-mountable device may take the form of or be similar in form to the eye-mountable device 610 and/or the eye-mountable device 710. For instance, the skin-mountable device may include a polymeric material that is the same or similar to any of the polymeric materials described herein and a substrate that is the same or similar to any of the substrates described herein.

IV. Conclusion

It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The invention claimed is:

1. A method comprising:
   forming a cross-linked polymer plug over a sensor located on a structure, such that the sensor is covered by the cross-linked polymer plug, wherein the sensor is configured to detect an analyte;
   forming a first polymer layer, wherein the first polymer layer defines a posterior side of an eye-mountable device;
   positioning the structure on the first polymer layer;
   forming a second polymer layer over the first polymer layer and the structure to provide a partially-fabricated device in which the structure is fully enclosed by the first polymer layer, the second polymer layer, and the cross-linked polymer plug, wherein the second polymer layer defines an anterior side of the eye-mountable device; and
   soaking the partially-fabricated device in a fluid, such that the cross-linked polymer plug swells out of the partially-fabricated device to leave a channel in the second polymer layer, wherein the sensor is configured to receive the analyte via the channel.

2. The method of claim 1, wherein forming a cross-linked polymer plug over a sensor located on a structure comprises injecting a polymerizable mixture over the sensor and curing the polymerizable mixture.

3. The method of claim 1, wherein forming a cross-linked polymer plug over a sensor located on a structure comprises spin coating a polymerizable mixture over the sensor and photopatterning the polymerizable mixture.

4. The method of claim 1, wherein the cross-linked polymer plug is formed by depositing a monomer, a cross-linking agent and an initiator to a surface of the sensor, and initiating polymerization.

5. The method of claim 4, wherein the monomer is a methacrylate monomer having a covalent bond to a side chain, where in the side chain comprises alkylene oxide units or 2-dimethylamino-ethane; and
   the cross-linking agent is poly(ethylene glycol) dimethacrylate.

6. The method of claim 4, wherein the monomer is a methacrylate macromonomer derived from the methacrylation of poly(vinylpyridine), poly(allylamine), or chitosan; and
   the cross-linking agent is poly(ethylene glycol) dimethacrylate.

7. The method of claim 1, wherein forming a second polymer layer over the first polymer layer and the structure comprises forming the second polymer layer in a mold comprising a molding piece.

8. The method of claim 7, wherein the cross-linked polymer plug is complaint, such that when the molding piece contacts the cross-linked polymer plug during formation of the second layer, the cross-linked plug deforms.

9. The method of claim 1, wherein the fluid comprises one or more fluids selected from the group consisting of an aqueous solution and an organic solvent.

10. The method of claim 1, wherein the fluid comprises an acid.

* * * * *